United States Patent
Colecraft et al.

(10) Patent No.: US 12,091,695 B2
(45) Date of Patent: *Sep. 17, 2024

(54) COMPOSITIONS AND METHODS FOR USING ENGINEERED DEUBIQUITINASES FOR PROBING UBIQUITIN-DEPENDENT CELLULAR PROCESSES

(71) Applicant: THE TRUSTEES OF COLUMBIA UNIVERSITY IN THE CITY OF NEW YORK, New York, NY (US)

(72) Inventors: Henry M. Colecraft, Robbinsville, NJ (US); Scott Kanner, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/501,967

(22) Filed: Nov. 3, 2023

(65) Prior Publication Data

US 2024/0067946 A1 Feb. 29, 2024

Related U.S. Application Data

(60) Division of application No. 16/867,923, filed on May 6, 2020, now Pat. No. 11,845,967, which is a continuation-in-part of application No. PCT/US2018/059229, filed on Nov. 5, 2018.

(60) Provisional application No. 62/582,108, filed on Nov. 6, 2017.

(51) Int. Cl.
| | |
|---|---|
| *C12N 9/64* | (2006.01) |
| *A61K 38/00* | (2006.01) |
| *C12N 15/85* | (2006.01) |
| *C12Q 1/6883* | (2018.01) |

(52) U.S. Cl.
CPC .......... *C12N 9/6472* (2013.01); *C12N 15/85* (2013.01); *C12Q 1/6883* (2013.01); *C12Y 304/22* (2013.01); *A61K 38/00* (2013.01); *C12Q 2600/156* (2013.01)

(58) Field of Classification Search
CPC .............................. C12N 9/6472; C12N 15/85
See application file for complete search history.

(56) References Cited

U.S. PATENT DOCUMENTS

| | | | |
|---|---|---|---|
| 2010/0129343 A1 | 5/2010 | Freissmuth et al. | |
| 2014/0220591 A1* | 8/2014 | Mevissen ............... | C12N 9/485 435/68.1 |
| 2015/0010525 A1* | 1/2015 | Wells ................. | G01N 33/6848 435/7.6 |

FOREIGN PATENT DOCUMENTS

WO 2016018921 A1 2/2016

OTHER PUBLICATIONS

Moss, et al. "Long QT syndrome: from channels to cardiac arrhythmias," J Clin Invest 115, 2018-2024, (2005).
Shimizu, et al. "The long QT syndrome: therapeutic implications of a genetic diagnosis," Cardiovasc Res 67, 347-356, (2005).
Tester, et al. "Compendium of cardiac channel mutations in 541 consecutive unrelated patients referred for long QT syndrome genetic testing," Heart Rhythm 2, 507-517, (2005).
Barhanin, et al. "K(V)LQT1 and IsK (minK) proteins associate to form the I(Ks) cardiac potassium current," Nature 384, 78-80, (1996).
Sanguinetti, et al. "Coassembly of K(V)LQT1 and minK (IsK) proteins to form cardiac I(Ks) potassium channel," Nature 384, 80-83, (1996).
Abbott, et al. "MiRP1 forms IKr potassium channels with HERG and is associated with cardiac arrhythmia," Cell 97, 175-187, (1999).
Curran, et al. "A molecular basis for cardiac arrhythmia: HERG mutations cause long QT syndrome," Cell 80, 795-803 (1995).
Grilo, et al. "Stereoselective Inhibition of the hERG1 Potassium Channel," Front Pharmacol 1, 137, (2010).
George, "Molecular and genetic basis of sudden cardiac death," J Clin Invest 123, 75-83, (2013).
Tester, et al. "Cardiomyopathie and channelopathic causes of sudden unexplained death in infants and children," Annu Rev Med 60, 69-84, (2009).
Peroz, et al. "Kv7.1 (KCNQ1) properties and channelopathies," J Physiol 586, 1785-1789, (2008).
Anderson, et al. "Large-scale mutational analysis of Kv11.1 reveals molecular insights into type 2 long QT syndrome," Nat Commun 5, 5535, (2014).
Aromolaran, et al. "LQT1 mutations KCNQ1 C-terminus assembly domain suppress IKs using different mechanisms," Cardiovasc Res 104, 501-511, (2014).
Kanki, et al. "A structural requirement for processing the cardiac K+ channel KCNQ1," J Biol Chem 279, 33976-33983, (2004).
Wiener, et al. "The KCNQ1 (Kv7.1) COOH terminus, a multitiered scaffold for subunit assembly and protein interaction," J Biol Chem 283, 5815-5830, (2008).
Hershko, et al. "The ubiquitin system," Annu Rev Biochem 67, 425-479, (1998).
Komander, "The emerging complexity of protein ubiquitination," Biochem Soc Trans 37, 937-953, (2009).
Heride, et al. "Ubiquitin code assembly and disassembly," Curr Biol 24, R215-220, (2014).
Foot, et al. "Ubiquitination and the Regulation of Membrane Proteins," Physiol Rev 97, 253-281, (2017).

(Continued)

*Primary Examiner* — Kevin E Weddington
(74) *Attorney, Agent, or Firm* — Bryan Cave Leighton Paisner LLP

(57) ABSTRACT

The present disclosure provides, inter alia, a recombinant engineered deubiquitinase (DUB) and methods for treating or ameliorating an inherited ion channelopathy, such as long QT syndrome, Brugada syndrome, or cystic fibrosis, in a subject. Further provided are methods for screening mutations causing such inherited ion channelopathies for a trafficking-deficient mutation that is treatable by the recombinant engineered DUB disclosed herein.

30 Claims, 27 Drawing Sheets
(25 of 27 Drawing Sheet(s) Filed in Color)

(56) References Cited

OTHER PUBLICATIONS

MacGurn, et al. "Ubiquitin and membrane protein turnover: from cradle to grave," Annu Rev Biochem 81, 231-259, (2012).
Mevissen, et al. "Mechanisms of Deubiquitinase Specificity and Regulation," Annu Rev Biochem 86, 159-192, (2017).
Mevissen, et al. "OTU deubiquitinases reveal mechanisms of linkage specificity and enable ubiquitin chain restriction analysis," Cell 154, 169-184 (2013).
Jespersen, et al. "The KCNQ1 potassium channel is down-regulated by ubiquitylating enzymes of the Nedd4/Nedd4-like family," Cardiovasc Res 74, 64-74, (2007).
Krzystanek, et al. "Deubiquitylating enzyme USP2 counteracts Nedd4-2-mediated downregulation of KCNQ1 potassium channels," Heart Rhythm 9, 440-448, (2012).
Albesa, et al. "Nedd4-2-dependent ubiquitylation and regulation of the cardiac potassium channel hERG1," J Mol Cell Cardiol 51, 90-98, (2011).
Hantouche, et al. "Bag1 Co-chaperone Promotes TRC8 E3 Ligase-dependent Degradation of Misfolded Human Ether a Go-Go-related Gene (hERG) Potassium Channels," J Biol Chem 292, 2287-2300, (2017).
Iwai, et al. "Hsp90 prevents interaction between CHIP and HERG proteins to facilitate maturation of wild-type and mutant HERG proteins," Cardiovasc Res 100, 520-528, (2013).
Guo, et al. "Extracellular K+ concentration controls cell surface density of IKr in rabbit hearts and of the HERG channel in human cell lines," J Clin Invest 119, 2745-2757, (2009).
Massaeli, et al. "Extracellular K+ is a prerequisite for the function and plasma membrane stability of HERG channels," Circ Res 106, 1072-1082, (2010).
Dennis, et al. "Antidepressant-induced ubiquitination and degradation of the cardiac potassium channel hERG," J Biol Chem 286, 34413-34425, (2011).
Kang, et al. "Regulation of the human ether-a-go-go-related gene (hERG) potassium channel by Nedd4 family interacting proteins (Ndfips)," Biochem J 472, 71-82, (2015).
Schneekloth, et al. "Chemical genetic control of protein levels: selective in vivo targeted degradation," J Am Chem Soc 126, 3748-3754, (2004).
Zhang, et al. "Chaperoned ubiquitylation—crystal structures of the Chip U box E3 ubiquitin ligase and a CHIP-Ubc13-Uev1a complex," Mol Cell 20, 525-538, (2005).
Murata, et al. "CHIP: a quality-control E3 ligase collaborating with molecular chaperones," Int J Biochem Cell Biol 35, 572-578 (2003).
Connell, et al. "The co-chaperone CHIP regulates protein triage decisions mediated by heat-shock proteins," Nat Cell Biol 3, 93-96, (2001).
Kubala, et al. "Structural and thermodynamic analysis of the GFP:GFP-nanobody complex," Protein Sci 19, 2389-2401, (2010).
Wang, et al. "Different HECT domain ubiquitin ligases employ distinct mechanisms of polyubiquitin chain synthesis," EMBO J 24, 4324-4333, (2005).
Wang, et al. "Molecular determinants of polyubiquitin linkage selection by an HECT ubiquitin ligase," EMBO J 25, 1710-1719, (2006).
Scialpi, et al. "Itch self-polyubiquitylation occurs through lysine-63 linkages," Biochem Pharmacol 76, 1515-1521, (2008).
Ogunjimi, et al. "The ubiquitin binding region of the Smurf HECT domain facilitates polyubiquitylation and binding of ubiquitylated substrates," J Biol Chem 285, 6308-6315, (2010).

Kim, et al. "Polyubiquitination by HECT E3s and the determinants of chain type specificity," Mol Cell Biol 29, 3307-3318, (2009).
Scheffner, et al. "Mammalian HECT ubiquitin-protein ligases: biological and pathophysiological aspects," Biochim Biophys Acta 1843, 61-74, (2014).
Michel, et al. "Assembly and specific recognition of k29- and k33-linked polyubiquitin," Mol Cell 58, 95-109, (2015).
Matsumoto, et al. "K11-linked polyubiquitination in cell cycle control revealed by a K11 linkagespecific antibody," Mol Cell 39, 477-484, (2010).
Newton, et al. "Ubiquitin chain editing revealed by polyubiquitin linkage-specific antibodies," Cell 134, 668-678, (2008).
Crabtree, et al. "Three-part inventions: intracellular signaling and induced proximity," Trends Biochem Sci 21, 418-422, (1996).
Inoue, et al. "An inducible translocation strategy to rapidly activate and inhibit small GTPase signaling pathways," Nat Methods 2, 415-418, (2005).
Yang, et al. "Genetically encoded molecules for inducibly inactivating CaV channels," Nat Chem Biol 3, 795-804, (2007).
Stornaiuolo, et al. "KDEL and KKXX retrieval signals appended to the same reporter protein determine different trafficking between endoplasmic reticulum, intermediate compartment, and Golgi complex," Mol Biol Cell 14, 889-902, (2003).
Lee, et al. "Targeting of the FYVE domain to endosomal membranes is regulated by a histidine switch," Proc Natl Acad Sci U S A 102, 13052-13057, (2005).
Maffucci, et al. "Specificity in pleckstrin homology (PH) domain membrane targeting: a role for a phosphoinositide-protein co-operative mechanism," FEBS Lett 506, 173-179 (2001).
Mevissen, et al. "Molecular basis of Lys11-polyubiquitin specificity in the deubiquitinase Cezanne," Nature 538, 402-405, (2016).
Damgaard, et al. "The Deubiquitinase OTULIN Is an Essential Negative Regulator of Inflammation and Autoimmunity," Cell 166, 1215-1230 e1220, (2016).
Ordureau, et al. "Quantifying ubiquitin signaling," Mol Cell 58, 660-676, (2015).
Kanner, et al. "Sculpting ion Channel Functional Expression with Engineered Ubiquitin Ligases," eLife. Dec. 19, 2017 vol. 6, pp. 1-26.
Kanner, et al. "Development of a High-Throughput Flow Cytometry Assay to Monitor Defective Trafficking and Rescue of Long QT2 Mutant hERG Channels," Frontiers in Physiology, Apr. 19, 2018, vol. 9, Article 397, pp. 1-10.
Extended European Search Report Application 18874097.1 dated Aug. 11, 2021.
Caussinus, et al. "Fluorescent fusion protein knockout mediated by anti-GFP nanobody," Nature Structural & Molecular Biology, Dec. 11, 2011, vol. 19, No. 1 pp. 117-122.
PCT/US2018/059229 International Search Report and Written Opinion dated Jan. 17, 2019.
Zhou, et al. "Original Article USP51 promotes deubiquitination and stabilization of ZEB1," Am J. Cancer Res, Jan. 1, 2017, pp. 2020-2031.
Imbrici, et al. "Therapeutic Approaches to Genetic Ion Channelopathies and Perspective in Drug Discovery," Frontiers in Pharmacology, vol. 7, May 10, 2016.
Kanner, et al. "Targeted deubiquitination rescues distinct trafficking-deficient ion channelopathies," Nature Methods, vol. 17, No. 12, Dec. 1, 2020, pp. 1245-1253.

\* cited by examiner

COMPOSITIONS AND METHODS FOR USING ENGINEERED DEUBIQUITINASES FOR PROBING UBIQUITIN-DEPENDENT CELLULAR PROCESSES

CROSS REFERENCE TO RELATED APPLICATIONS

The present application is a divisional of U.S. patent application Ser. No. 16/867,923, filed on May 6, 2020, which is a continuation in part of PCT international application no. PCT/US2018/059229, filed on Nov. 5, 2018, which claims benefit of U.S. Provisional Patent Application Ser. No. 62/582,108, filed on Nov. 6, 2017. The entire contents of the aforementioned applications are incorporated by reference as if recited in full herein.

GOVERNMENT FUNDING

This invention was made with government support under grant no. HL122421, awarded by the National Institutes of Health. The government has certain rights in the invention.

FIELD OF THE DISCLOSURE

The present disclosure provides, inter alia, a recombinant engineered deubiquitinase (DUB) and methods for treating or ameliorating an inherited ion channelopathy, such as long QT syndrome, Brugada syndrome, or cystic fibrosis, in a subject. Methods for screening mutations causing such inherited ion channelopathies for a trafficking-deficient mutation that is treatable by the recombinant engineered DUB disclosed above, are also provided herein.

BACKGROUND OF THE DISCLOSURE

Integral surface membrane proteins including ion channels, transporters, and receptors are vital to the survival and function of all cells. Consequently, processes that control the surface abundance and composition of membrane proteins are critical determinants of cellular biology and physiology. Impaired surface trafficking of membrane proteins underlies diverse diseases ranging from cystic fibrosis to cardiac arrhythmias (Gelman & Kopito, 2002; Anderson et al., 2014), motivating a need to better understand fundamental mechanisms controlling membrane protein surface density. The surface repertoire of membrane proteins is regulated by multi-layered maturation and trafficking processes; starting with proper folding in the endoplasmic reticulum (ER), post-translational maturation in the Golgi apparatus, delivery to and continuous refinement at the surface, and ultimately, their removal and degradation in lysosomes (MacGurn et al., 2012; Foot et al., 2017). Basic understanding of the mechanisms that control these diverse aspects of membrane protein fate is an important and intensely studied research area.

Ubiquitination is a powerful mechanism capable of tuning membrane protein functional expression by regulating multiple steps in the membrane protein lifecycle. Ubiquitin is a 76-residue protein that can be covalently attached to lysine residues on polypeptide substrates through the sequential action of three enzymes: a ubiquitin activation enzyme (E1); a ubiquitin-conjugating enzyme (E2); and a ubiquitin ligase (E3), that catalyzes transfer of ubiquitin to substrates. The human genome encodes 2 E1s, 37 E2s, and >600 E3 ubiquitin ligases. Ubiquitin contains seven lysine residues (K6, K11, K27, K29, K33, K48, K63) that, together with its N-terminus methionine (Met1), can serve as secondary attachment points to make diverse polyubiquitin chains with different structures and functions (Komander, 2009) (FIG. 1). Ubiquitination has classically been ascribed to targeting cytosolic proteins for degradation by the proteasome (Hershko & Ciechanover, 1998). In contrast, ubiquitination of membrane proteins can lead to more nuanced outcomes including regulating protein trafficking/sorting, stability, and/or function (Komander, 2009; Foot et al., 2017). Ubiquitination has been associated with inherited disorders such as cystic fibrosis, cardiac arrhythmias, epilepsy, and neuropathic pain, as well as infectious disease, contributing to the pathogenic lifecycle of diverse viral and bacterial pathogens.

Deubiquitinases (DUBs) are specialized isopeptidases that provide salience to ubiquitin signaling through the revision and removal of ubiquitin chains. There are over 100 human DUBs, comprising 6 distinct families: 1) the ubiquitin specific proteases (USP) family, 2) the ovarian tumor proteases (OUT) family, 3) the ubiquitin C-terminal hydrolases (UCH) family, 4) the Josephin domain family (Josephin), 5) the motif interacting with ubiquitin-containing novel DUB family (MINDY), and 6) the JAB1/MPN/Mov34 metalloenzyme domain family (JAMM). Of note, the USP family is relatively promiscuous, hydrolyzing all ubiquitin linkages, in stark contrast to the OTU family, which contains a diverse set of enzymes with distinct linkage preferences. Linkage-specific DUBs have recently been purified and used in cell-free in vitro assays as a way to diagnose chain specificity before running target proteins on Western blot. Moreover, purified linkage-specific DUBs have been used to sculpt more atypical ubiquitin chains for isolation and structural analysis.

Inherited ion channelopathies are rare diseases that encompass a broad range of disorders in the nervous system (epilepsy, migraine, neuropathic pain), cardiovascular system (long QT syndrome, Brugada syndrome), respiratory (cystic fibrosis), endocrine (diabetes, hyperinsulinemic hypoglycemia), and urinary (Bartter syndrome, diabetes insipidus) system. The rapidly expanding field of next generation genomic sequencing has revealed thousands of channel mutations, with diverse underlying mechanisms. Understanding the underlying cause of loss-of-function is critical for employing a personalized strategy to treat each disease. A vast number of these inherited mutations result in channels with defects in trafficking to the surface membrane. For example, cystic fibrosis, the most common lethal genetic disease in Caucasians arises due to defects in the cystic fibrosis transmembrane conductance regulator (CFTR), a chloride ion channel. The most studied mutation ($\Delta$F508), accounts for ~85% of all cases, and causes channel misfolding and ubiquitin-dependent trafficking defects. In the case of Long QT Syndrome, over 500 mutations in two channels (KCNQ1, hERG) encompass nearly 90% of all inherited cases. Trafficking deficits in the two channels is the mechanistic basis for a majority of the disease-causing mutations. It would be beneficial to have a platform for high-throughput screening of such disease-causing mutations to diagnose underlying pathological mechanisms. This diagnostic capability would inform on the best treatment options for particular mutations, thereby advancing personalized medicine for these rare diseases. The disclosure provided herein relates to such platform. In addition, the disclosure provides a novel therapeutic opportunity for gene therapy and targeted correction of ubiquitin-dependent trafficking defects that are uncovered.

Further, the recent Ebola epidemic and emergence of drug-resistant 'super-bugs' have uncovered the growing need for quick, generalizable approaches for containment and limiting spread of infection. Infectious pathogens exploit host cellular processes of ubiquitination in order to propagate and spread disease. In particular, viruses have been shown to exploit ubiquitin in every aspect of their life cycle: viral entry, replication, and budding. Across viral families, many contain proteins with PY motifs allowing recruitment of host ubiquitin E3 ligases. The present disclosure takes advantage of this conserved mechanism to provide a generalizable approach to selectively target diverse infectious processes. In effect, this disclosure is able to combat the viral reliance on ubiquitination necessary for sustaining infection and provides a modular and transferrable approach for battling emerging, life-threatening and/or chronic infections.

SUMMARY OF THE DISCLOSURE

The present disclosure provides a recombinant engineered deubiquitinase (DUB) comprising:
  a) a catalytic unit;
  b) a protein binder; and
  c) a variable linker between the catalytic unit and the protein binder.

The present disclosure also provides a method of treating or ameliorating the effects of an inherited ion channelopathy in a subject, comprising administering to the subject a nucleic acid encoding the recombinant engineered DUB aforementioned.

The present disclosure also provides a method of screening mutations causing an inherited ion channelopathy for a trafficking-deficient mutation that is treatable by the recombinant engineered DUB aforementioned, comprising the steps of:
  a) in cells expressing a mutation causing an inherited ion channelopathy, measuring surface density and/or total expression of the mutant channel;
  b) if the surface density and/or total expression of the mutant channel is decreased relative to a wild-type (WT) channel, determining the ubiquitination status of the mutant channel;
  c) based on the ubiquitination status of the mutant channel, selecting a recombinant engineered DUB aforementioned and co-expressing it with the mutation, then measuring surface density and/or total expression of the mutant channel in cells with the co-expression; and
  d) identifying the mutation as treatable if the surface density and/or total expression of the mutant channel in step (c) is recovered relative to the WT channel.

The present disclosure also provides a method of treating or ameliorating the effects of acute/chronic viral infections in a subject, comprising administering to the subject a nucleic acid encoding the recombinant engineered DUB aforementioned.

The present disclosure also provides a recombinant expression vector comprising a nucleic acid that encodes the recombinant engineered DUB aforementioned, and further provides a cell transformed with said vector.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

FIG. 6A shows the structure of full-length CFTR channel (PDB: 5UAK). NBD1 highlighted in red.

FIG. 6B shows whole cell patch clamp recordings in Fischer Rat Thyroid (FRT) epithelial cells stably expressing WT or mutant F508del CFTR channels. Population current-voltage response curves for forskolin-activated WT (circle, black) and F508del (square, red) cells, compared to forskolin-activated, Orkambi-treated F508del cells with nano alone (triangle, green) or with enDUB (inverted triangle, blue).

FIG. 6C is same as FIG. 6B but with FRT cells stably expressing WT or N1303K CFTR channels. **$p<0.005$, two-way ANOVA with Tukey's comparison.

FIG. 6D shows maturation of human bronchial epithelial cells (HBECs) cultured at air-liquid interface (ALI) (left; H&E), featuring a pseudostratified epithelium with mucin-containing goblet cells (*) (middle; Alcian Blue). Apical (ap) and basal (bs) compartments labeled.

FIG. 6E shows immunofluorescence (IF) staining of mature ALI cultures, featuring ciliated cells (green; acetylated-tubulin), mucin-containing goblet cells (pink; MUCSAC), and basal cell layer (red; CK5), merged with DAPI staining (blue; nuclei).

FIG. 6F shows anti-CFTR IF staining of transverse cryosections from WT donor HBECs and F508del homozygous patient hBECs cultured at ALI (heatmap; CFTR). VX809 is lumacaftor, the active pharmacologic chaperone (or corrector) found in Orkambi. White box and inset highlights CFTR expression at the apical membrane.

FIG. 6G shows quantification of apical CFTR density from confocal images (H). **$p<0.0001$, one-way ANOVA with Tukey's comparison.

FIG. 7A shows the structure of full-length KCNQ1 channel (PDB: 5VMS).

FIG. 7B shows confocal image of adult guinea pig cardiomyocytes expressing WT KCNQ1-YFP (left) or G589D-YFP (right).

FIG. 7C shows representative action potential recordings from cardiomyocytes expressing WT KCNQ1-YFP (left) or G589D-YFP (right)+nano alone (red) or enDUB (blue).

FIG. 7D shows quantification of action potential duration at 90% repolarization (APD90). **$p<0.0002$, one-way ANOVA with Tukey's comparison.

DETAILED DESCRIPTION OF THE DISCLOSURE

Figure 1:
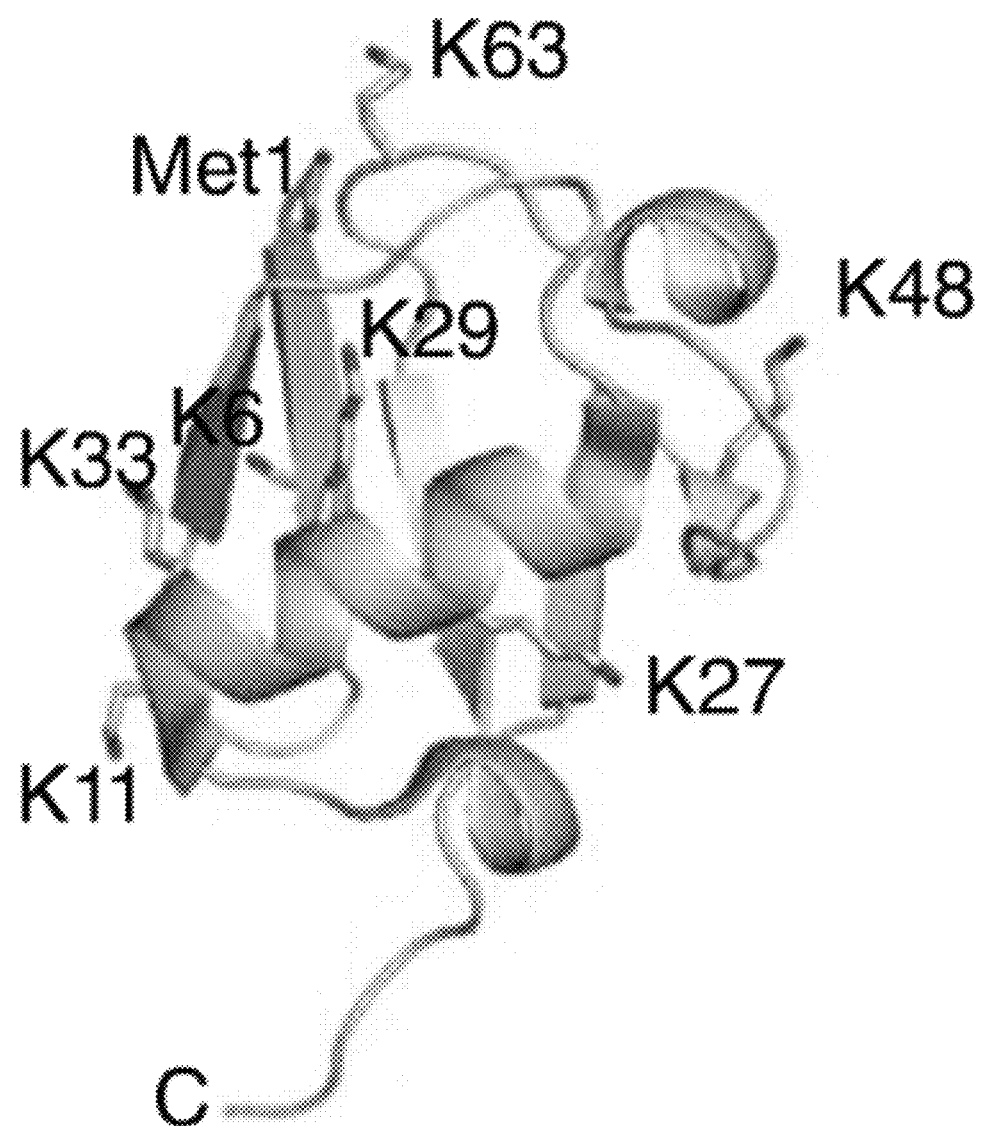
FIG. 1 shows the structure of ubiquitin, including seven lysine residues (K6, K11, K27, K29, K33, K48, K63), together with its N-terminus methionine (Met1).

One embodiment of the present disclosure is a recombinant engineered deubiquitinase (DUB) comprising:
a) a catalytic unit;
b) a protein binder; and
c) a variable linker between the catalytic unit and the protein binder.

In one aspect of this embodiment, the catalytic unit of the recombinant engineered DUB is selective for all ubiquitin linkage types. In another aspect of this embodiment, the catalytic unit is selective for particular ubiquitin linkage type.

According to this embodiment, the catalytic unit comprises the catalytic domain of a deubiquitinase selected from the ubiquitin specific proteases (USP) family, the ovarian tumor proteases (OTU) family, the ubiquitin C-terminal hydrolases (UCH) family, the Josephin domain family (Josephin), the motif interacting with ubiquitin-containing novel DUB family (MINDY), and the JAB1/MPN/Mov34 metalloenzyme domain family (JAMM).

According to some embodiments, the catalytic unit comprises the catalytic domain of a deubiquitinase from the USP family. In one embodiment, the catalytic unit comprises the catalytic domain of USP21.

According to some embodiments, the catalytic unit comprises the catalytic domain of a deubiquitinase from the OTU family. In one embodiment, the catalytic unit comprises the catalytic domain of OTUD1. In one embodiment, the catalytic unit comprises the catalytic domain of OTUD4. In one embodiment, the catalytic unit comprises the catalytic domain of Cezanne. In one embodiment, the catalytic unit comprises the catalytic domain of TRABID. In one embodiment, the catalytic unit comprises the catalytic domain of OTULIN.

According to this embodiment, the protein binder of the recombinant engineered DUB is selected from intracellular antibody fragments, scFvs, nanobodies, antibody mimetics, monobodies, DARPins, lipocalins, and targeting sequences. In one embodiment, the protein binder is a vhh4 nanobody.

In certain embodiments, the catalytic unit is the catalytic domain of USP21, and the protein binder is vhh4 nanobody, and the resulting recombinant engineered deubiquitinase (nanoUSP21) is capable of non-selectively eliminating all linkage types. In certain embodiments, the catalytic unit is the catalytic domain of OTUD1, and the protein binder is vhh4 nanobody, and the resulting recombinant engineered deubiquitinase (nanoOTUD1) is capable of selectively eliminating K63 linkage. In certain embodiments, the catalytic unit is the catalytic domain of OTUD4, and the protein binder is vhh4 nanobody, and the resulting recombinant engineered deubiquitinase (nanoOTUD4) is capable of selectively eliminating K48 linkage. In certain embodiments, the catalytic unit is the catalytic domain of Cezanne, and the protein binder is vhh4 nanobody, and the resulting recombinant engineered deubiquitinase (nanoCezanne) is capable of selectively eliminating K11 linkage. In certain embodiments, the catalytic unit is the catalytic domain of TRABID, and the protein binder is vhh4 nanobody, and the resulting recombinant engineered deubiquitinase (nanoTRABID) is capable of selectively eliminating K29 and/or K33 linkages. In certain embodiments, the catalytic unit is the catalytic domain of OTULIN, and the protein binder is vhh4 nanobody, and the resulting recombinant engineered deubiquitinase (nanoOTULIN) is capable of selectively eliminating Met1 linkage. As used herein, "capable of" means that the subject, e.g. recombinant engineered DUB, is fully functional and under the proper conditions, will carry out the stated functions.

Another embodiment of the present disclosure is a method of treating or ameliorating the effects of an inherited ion channelopathy in a subject, comprising administering to the subject a nucleic acid encoding the recombinant engineered DUB previously disclosed herein.

As used herein, the term "inherited ion channelopathy" refers to rare diseases that encompass a broad range of disorders in the nervous system, cardiovascular system, respiratory system, endocrine system, and urinary system. In the present disclosure, an "inherited ion channelopathy" includes but is not limited to: epilepsy, migraine, neuropathic pain, cardiac arrhythmias, long QT syndrome, Brugada syndrome, cystic fibrosis, diabetes, hyperinsulinemic hypoglycemia, Bartter syndrome, and diabetes insipidus. In preferred embodiments, the inherited ion channelopathy is long QT syndrome.

In a preferred embodiment, the inherited ion channelopathy is long QT syndrome, and the recombinant engineered deubiquitinase is nanoOTUD1.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

As used herein, the terms "ameliorate", "ameliorating" and grammatical variations thereof mean to decrease the severity of the symptoms of a disease in a subject, preferably a human.

As used herein, "administration," "administering" and variants thereof means introducing a composition, such as a synthetic membrane-receiver complex, or agent into a subject and includes concurrent and sequential introduction of a composition or agent. The introduction of a composition or agent into a subject is by any suitable route, including orally, pulmonarily, intranasally, parenterally (intravenously, intramuscularly, intraperitoneally, or subcutaneously), rectally, intralymphatically, or topically. Administration includes self-administration and the administration by another. A suitable route of administration allows the composition or the agent to perform its intended function. For example, if a suitable route is intravenous, the composition is administered by introducing the composition or agent into a vein of the subject. Administration can be carried out by any suitable route.

As used herein, a "subject" is a mammal, preferably, a human. In addition to humans, categories of mammals within the scope of the present disclosure include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc.

Another embodiment of the present disclosure is a method of screening mutations causing an inherited ion channelopathy for a trafficking-deficient mutation that is treatable by the recombinant engineered DUB previously disclosed herein, comprising the steps of:
a) in cells expressing a mutation causing an inherited ion channelopathy, measuring surface density and/or total expression of the mutant channel;
b) if the surface density and/or total expression of the mutant channel is decreased relative to a wild-type (WT) channel, determining the ubiquitination status of the mutant channel;
c) based on the ubiquitination status of the mutant channel, selecting a recombinant engineered DUB of claim 1 and co-expressing it with the mutation, then measuring surface density and/or total expression of the mutant channel in cells with the co-expression; and
d) identifying the mutation as treatable if the surface density and/or total expression of the mutant channel in step (c) is recovered relative to the WT channel.

Another embodiment of the present disclosure is a method of treating or ameliorating the effects of acute/chronic viral infections in a subject, comprising administering to the subject a nucleic acid encoding the recombinant engineered DUB previously disclosed herein.

In some aspects of this and other embodiments, the subject is a mammal. Preferably, the mammal is selected from the group consisting of humans, primates, farm animals, and domestic animals. More preferably, the mammal is a human.

Another embodiment of the present disclosure is a recombinant expression vector comprising a nucleic acid that encodes the recombinant engineered DUB previously disclosed herein.

Another embodiment of the present disclosure is a cell transformed with the vector disclosed above.

Additional Definitions

The term "amino acid" means naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. An "amino acid analog" means compounds that have the same basic chemical structure as a naturally occurring amino acid, e.g., a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Imino acids such as, e.g., proline, are also within the scope of "amino acid" as used here. An "amino acid mimetic" means a chemical compound that has a structure that is different from the general chemical structure of an amino acid, but that functions similarly to a naturally occurring amino acid.

As used herein, the terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymers.

"Nucleic acid" or "oligonucleotide" or "polynucleotide" used herein means at least two nucleotides covalently linked together. Many variants of a nucleic acid may be used for the same purpose as a given nucleic acid. Thus, a nucleic acid also encompasses substantially identical nucleic acids and complements thereof.

Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be synthesized as a single stranded molecule or expressed in a cell (in vitro or in vivo) using a synthetic gene. Nucleic acids may be obtained by chemical synthesis methods or by recombinant methods.

The nucleic acid may also be an RNA such as an mRNA, tRNA, short hairpin RNA (shRNA), short interfering RNA (siRNA), double-stranded RNA (dsRNA), transcriptional gene silencing RNA (ptgsRNA), Piwi-interacting RNA, pri-miRNA, pre-miRNA, micro-RNA (miRNA), or anti-miRNA.

As used herein, the term "antibody" encompasses an immunoglobulin whether natural or partly or wholly synthetically produced, and fragments thereof. The term also covers any protein having a binding domain which is homologous to an immunoglobulin binding domain. These proteins can be derived from natural sources, or partly or wholly synthetically produced. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies; murine antibodies; chimeric, mouse-human, mouse-primate, primate-human monoclonal antibodies, anti-idiotype antibodies, antibody fragments, such as, e.g., scFv, (scFv)2, Fab, Fab', and F(ab')2, F(ab1)2, Fv, dAb, and Fd fragments, diabodies, nanobodies and antibody-related polypeptides. Antibody includes bispecific antibodies and multispecific antibodies so long as they exhibit the desired biological activity or function.

The term "antigen binding fragment" used herein refers to fragments of an intact immunoglobulin, and any part of a polypeptide including antigen binding regions having the ability to specifically bind to the antigen. For example, the antigen binding fragment may be a F(ab')2 fragment, a Fab' fragment, a Fab fragment, a Fv fragment, or a scFv fragment, but is not limited thereto. A Fab fragment has one antigen binding site and contains the variable regions of a light chain and a heavy chain, the constant region of the light chain, and the first constant region CH1 of the heavy chain. A Fab' fragment differs from a Fab fragment in that the Fab' fragment additionally includes the hinge region of the heavy chain, including at least one cysteine residue at the C-terminal of the heavy chain CH1 region. The F(ab')2 fragment is produced whereby cysteine residues of the Fab' fragment are joined by a disulfide bond at the hinge region. A Fv fragment is the minimal antibody fragment having only heavy chain variable regions and light chain variable regions, and a recombinant technique for producing the Fv fragment is well known in the art. Two-chain Fv fragments may have a structure in which heavy chain variable regions are linked to light chain variable regions by a non-covalent bond. Single-chain Fv (scFv) fragments generally may have a dimer structure as in the two-chain Fv fragments in which heavy chain variable regions are covalently bound to light chain variable regions via a peptide linker or heavy and light chain variable regions are directly linked to each other at the C-terminal thereof. The antigen binding fragment may be obtained using a protease (for example, a whole antibody is digested with papain to obtain Fab fragments, and is digested with pepsin to obtain F(ab')2 fragments), and may be prepared by a genetic recombinant technique. A dAb fragment consists of a VH domain. Single-chain antibody molecules may comprise a polymer with a number of individual molecules, for example, dimmer, trimer or other polymers.

"Vector" used herein refers to an assembly which is capable of directing the expression of desired protein. The vector must include transcriptional promoter elements which are operably linked to the gene(s) of interest. The vector may be composed of either deoxyribonucleic acids ("DNA"), ribonucleic acids ("RNA"), or a combination of the two (e.g., a DNA-RNA chimeric). Optionally, the vector may include a polyadenylation sequence, one or more restriction sites, as well as one or more selectable markers such as neomycin phosphotransferase or hygromycin phosphotransferase. Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

As used herein, the terms "cell", "host cell" or "recombinant host cell" refers to host cells that have been engineered to express a desired recombinant protein. Methods of creating recombinant host cells are well known in the art. For example, see Sambrook et al. (MOLECULAR CLONING: A LABORATORY MANUAL (Sambrook et al, eds., Cold Spring Harbor Laboratory Press, Cold Spring Harbor, 1989), Ausubel et al. (CURRENT PROTOCOLS IN MOLECULAR BIOLOGY Ausubel et al., eds., John Wiley & Sons, New York, 1987). In the present disclosure, the host cells are transformed with the vectors described herein.

Recombinant host cells as used herein may be any of the host cells used for recombinant protein production, including, but not limited to, bacteria, yeast, insect and mammalian cell lines.

As used herein, the term "increase," "enhance," "stimulate," and/or "induce" (and like terms) generally refers to the act of improving or increasing, either directly or indirectly, a concentration, level, function, activity, or behavior relative to the natural, expected, or average, or relative to a control condition.

As used herein, the term "inhibit," "suppress," "decrease," "interfere," and/or "reduce" (and like terms) generally refers to the act of reducing, either directly or indirectly, a concentration, level, function, activity, or behavior relative to the natural, expected, or average, or relative to a control condition.

The terminology used herein is for the purpose of describing particular embodiments only and is not intended to be limiting. As used in the specification and the appended claims, the singular forms "a," "an," and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

The following examples are provided to further illustrate certain aspects of the present disclosure. These examples are illustrative only and are not intended to limit the scope of the disclosure in any way.

EXAMPLES

Example 1

Materials and Methods

Molecular Biology and Cloning of Plasmid Vectors

A customized bicistronic vector (xx-P2A-CFP) was synthesized in the pUC57 vector, in which coding sequence for P2A peptide was sandwiched between an upstream multiple cloning site and enhanced cyan fluorescent protein (CFP) (Genewiz). The xx-P2A-CFP fragment was amplified by PCR and cloned into the PiggyBac CMV mammalian expression vector (System Biosciences) using NheI/NotI sites. To generate nano-xx-P2A-CFP, we PCR amplified the coding sequence for GFP nanobody (vhhGFP4) and cloned it into xx-P2A-CFP using NheI/AflIII sites. The nanoDUB construct was created by gene synthesis (Genewiz), and featured the coding sequence for GFP nanobody (vhhGFP4) (Kubala et al., 2010) in frame with the catalytic domain of a selected deubiquitinase (DUB), separated by a flexible GSG linker. This fragment was amplified by PCR and cloned into the xx-P2A-CFP vector using NheI/AflIII sites.

Slmb:nano-P2A-CFP was derived from pcDNA3_NSlmb-vhhGFP4 (Addgene #35579) (Caussinus et al., 2011). We PCR amplified the NSlmb-vhhGFP4 fragment and cloned it into xx-P2A-CFP using NheI/AflIII sites. To generate nanoMDM2, we PCR amplified the RING domain (residues 432-491) and cloned this fragment into nano-xx-P2A-CFP using AscI/AflIII sites. To create nanoNEDD4L we first PCR amplified the HECT domain (residues 640-975) of NEDD4L (PCI_NEDD4L; Addgene #27000) and cloned this fragment into nano-xx-P2A-CFP using AscI/AflIII sites. The resulting construct, nanoNEDD4L-P2A-CFP expressed poorly so we swapped positions of the nanoNEDD4L and CFP. We first generated CFP-P2A-xx and then PCR amplified nanoNEDD4L. The resulting fragment was cloned into CFP-P2A-xx using BglII/NotI sites.

KCNQ1/E1 constructs were made as described previously (Aromolaran et al., 2014). Briefly, overlap extension PCR was used to fuse enhanced yellow fluorescent proteins (EYFP) in frame to the C-terminus of KCNQ1 and KCNE1. A 13-residue bungarotoxin-binding site (BBS; TGGCGGTACTACGAGAGCAGCCTGGAGCCC-TACCCCGAC) (Sekine-Aizawa & Huganir, 2004; Yang et al., 2010) was introduced between residues 148-149 in the extracellular S1-S2 loop of KCNQ1 using the Quik-Change Lightning Site-Directed Mutagenesis Kit (Stratagene) according to the manufacturer's instructions.

The nanoDUB construct (DUB-P2A-CFP-P2A:nano) was created in three parts. First, DUB-P2A-CFP was created by PCR amplifying the DUB catalytic domain and cloning the amplified fragment into xx-P2A-CFP vector using AscI/AflII sites. Second, we used overlap extension PCR to create a P2A:nano cassette which was then cloned downstream of CFP in the DUB-P2A-CFP construct using BglII/NotI sites, generating DUB-P2A-CFP-P2A-nano.

Generation of Adenoviral Vectors

Low passage human embryonic kidney (HEK293) cells were cultured at 37° C. in DMEM supplemented with 8% fetal bovine serum (FBS) and 100 mg/mL of penicillin-streptomycin. HEK293 cell transfection was accomplished using the calcium phosphate precipitation method. Briefly, plasmid DNA was mixed with 62 μL of 2.5M $CaCl_2$) and sterile deionized water (to a final volume of 500 μL). The mixture was added dropwise, with constant tapping to 500 μL of 2× Hepes buffered saline containing (in mM): Hepes 50, NaCl 280, $Na_2HPO_4$ 1.5, pH 7.09. The resulting DNA-calcium phosphate mixture was incubated for 20 min at room temperature and then added dropwise to HEK293 cells (60-80% confluent). Cells were washed with $Ca^{2+}$-free phosphate buffered saline after 4-6 h and maintained in supplemented DMEM.

Chinese hamster ovary (CHO) cells were cultured at 37° C. in Kaighn's Modified Ham's F-12K (ATCC) supplemented with 8% FBS and 100 mg/mL of penicillin-streptomycin. CHO cells were transiently transfected with desired constructs in 35 mm tissue culture dishes-KCNQ1 (0.5 μg), KCNE1 (0.5 μg), and nano-P2A-CFP (0.5 μg), and nanoDUB-P2A-CFP (0.5 μg) using X-tremeGENE HP (1:2 DNA/reagent ratio) according to the manufacturers' instructions (Roche).

Primary cultures of adult rat heart ventricular cells were prepared as previously described (Colecraft et al., 2002; Subramanyam et al., 2013), in accordance with the guidelines of Columbia University Animal Care and Use Committee. Adult male Sprague-Dawley rats were euthanized with an overdose of isoflurane. Hearts were excised and ventricular myocytes isolated by enzymatic digestion with 1.7 mg Liberase-TM enzyme mix (Roche) using a Langendorff perfusion apparatus. Healthy rod-shaped myocytes were cultured in Medium 199 (Life Technologies) supplemented with (in mM) carnitine (5), creatine (5), taurine (5) penicillin-streptomycin-glutamine (0.5%, Life technologies), and 5% (vol/vol) FBS (Life Technologies) to promote attachment to dishes. After 5 h, the culture medium was switched to Medium 199 with 1% (vol/vol) serum, but otherwise supplemented as described above. Cultures were maintained in humidified incubators at 37° C. and 5% CO2.

Flow Cytometry Assay of Total and Surface Q1 Channels

Cell surface and total ion channel pools were assayed by flow cytometry in live, transfected HEK293 cells as previously described (Yang et al., 2010; Aromolaran et al., 2014). Briefly, 48 h post-transfection, cells cultured in 6-well plates gently washed with ice cold PBS containing $Ca^{2+}$ and $Mg^{2+}$ (in mM: 0.9 $CaCl_2$), 0.49 $MgCl_2$, pH 7.4), and then incubated for 30 min in blocking medium (DMEM with 3% BSA) at 4° C. HEK293 cells were then incubated with 1 μM Alexa Fluor 647 conjugated α-bungarotoxin (BTX-647; Life Technologies) in DMEM/3% BSA on a rocker at 4° C. for 1 h, followed by washing three times with PBS (containing $Ca^{2+}$ and $Mg^{2+}$). Cells were gently harvested in $Ca^{2+}$-free PBS, and assayed by flow cytometry using a BD LSRII Cell Analyzer (BD Biosciences, San Jose, CA, USA). CFP- and YFP-tagged proteins were excited at 407 and 488 nm, respectively, and Alexa Fluor 647 was excited at 633 nm.

Optical pulse chase assays to monitor rates of channel forward trafficking and internalization were conducted on live, transfected HEK293 cells. Cells were placed on 4° C. to halt trafficking processes and washed twice with PBS containing $Ca^{2+}$ and $Mg^{2+}$. For forward trafficking experiments, cells were incubated with 5 μM untagged BTX in DMEM/3% BSA at 4° C. for 1 h to block surface channels, and then washed three times with PBS containing $Ca^{2+}$ and $Mg^{2+}$. Cells were incubated with DMEM/3% BSA and placed at 37° C. to resume trafficking for different time intervals (0, 5, 10, 20, 40, 60 min). Cells were then returned to 4° C. and newly delivered channels were labeled with 1 μM BTX-647 in DMEM/3% BSA for 1 h. Finally, cells were washed three times with PBS containing $Ca^{2+}$ and $Mg^{2+}$, gently harvested in $Ca^{2+}$-free PBS, and assayed by flow cytometry. For internalization experiments, cells were incubated in DMEM/3% BSA blocking medium for 30 min at 4° C., followed by a pulse of 1 μM biotinylated α-bungarotoxin (BTX-biotin; Life Technologies) for 1 h with gentle rocking at 4° C. Cells were washed three times in PBS containing $Ca^{2+}$ and $Mg^{2+}$ and placed in DMEM/3% BSA at 37° C. for different time intervals (0, 5, 10, 20, 40, 60 min) to resume trafficking. Cells were returned to 4° C., washed once with PBS, and channels remaining at the surface were labeled with streptavidin-conjugated Alexa Fluor (Life Technologies). Finally, cells were washed twice more with PBS with $Ca^{2+}$ and $Mg^{2+}$, harvested in $Ca^{2+}$-free PBS, and assayed by flow cytometry.

Confocal Detection of Total and Surface Q1 Expression in Cardiomyocytes

At 48 h post-infection, adult rat cardiomyocytes cultured on 35 mm MatTek dishes (MatTek Corporation) were gently washed with M199 media (with 0.9 mM $CaCl_2$), 0.49 mM $MgCl_2$, pH 7.4) and fixed with 4% paraformaldehyde (PFA) for 10 min at room temperature (RT). Cardiomyocytes were washed three times with PBS, and incubated for 30 min in blocking medium (M199 with 3% BSA). Cardiomyocytes were then incubated with 1 μM BTX-biotin in M199/3% BSA at room temperature for 1 h followed by washing three times with PBS to remove unbound biotinylated BTX. Cells were then incubated with 10 nM streptavidin-conjugated quantum dot 655 (QD655; Life Technologies) for 1 h at 4° C. in the dark, washed three times with PBS, and imaged with Nikon Ti Eclipse inverted microscope for scanning confocal microscopy.

Electrophysiology

For potassium channel measurements, whole-cell membrane currents were recorded at room temperature in CHO cells using an EPC-10 patch-clamp amplifier (HEKA Electronics) controlled by the PatchMaster software (HEKA). A coverslip with adherent CHO cells was placed on the glass bottom of a recording chamber (0.7-1 mL in volume) mounted on the stage of an inverted Nikon Eclipse Ti-U microscope. Micropipettes were fashioned from 1.5 mm thin-walled glass and fire-polished. Internal solution contained (mM): 133 KCl, 0.4 GTP, 10 EGTA, 1 $MgSO_4$, 5 $K_2ATP$, 0.5 $CaCl_2$), and 10 HEPES (pH 7.2). External solution contained (in mM): 147 NaCl, 4 KCl, 2 $CaCl_2$), and 10 HEPES (pH 7.4). Pipette resistance was typically 1.5 MO when filled with internal solution. I-V curves were generated from a family of step depolarizations (−40 to +100 mV in 10 mV steps from a holding potential of −50 mV). Currents were sampled at 20 kHz and filtered at 5 kHz. Traces were acquired at a repetition interval of 10 s.

For calcium channel measurements, whole-cell recordings were carried out in HEK293 cells at room temperature. Internal solution contained (mM): 135 Cs Methanesulfonate, 5 CsCl, 5 EGTA, 1 $MgCl_2$, 4 MgATP, 10 HEPES (pH 7.2). External solution contained (mM): 140 tetraethylammonium-methanesulfonate, 5 BaCl$_2$, 10 HEPES (pH 7.4). Leak and capacitive currents were subtracted using a P/4 protocol. I-V curves were generated from a family of step depolarizations (−60 to +100 mV in 10 mV steps from a holding potential of −90 mV). Currents were sampled at 20 kHz and filtered at 5 kHz. Traces were acquired at a repetition interval of 10 s.

Immunoprecipitation and Western Blotting

HEK293 cells were washed once with PBS without Ca$^{2+}$, harvested, and resuspended in RIPA lysis buffer containing (in mM) Tris (20, pH 7.4), EDTA (1), NaCl (150), 0.1% (wt/vol) SDS, 1% Triton X-100, 1% sodium deoxycholate and supplemented with protease inhibitor mixture (10 μL/mL, Sigma-Aldrich), PMSF (1 mM, Sigma-Aldrich), and PR-619 deubiquitinase inhibitor (50 μM, LifeSensors). Lysates were prepared by incubation at 4° C. for 1 h, with occasional vortex, and cleared by centrifugation (10,000×g, 10 min, 4° C.). Supernatants were transferred to new tubes, with aliquots removed for quantification of total protein concentration determined by the bis-cinchonic acid protein estimation kit (Pierce Technologies). Lysates were precleared by incubation with 10 μL Protein A/G Sepharose beads (Rockland) for 40 min at 4° C. and then incubated with 0.75 μg anti-Q1 (Alomone) for 1 h at 4° C. Equivalent total protein amounts were added to spin-columns containing 25 μL Protein A/G Sepharose beads, tumbling overnight at 4° C. Immunoprecipitates were washed 3-5 times with RIPA buffer, spun down at 500×g, eluted with 40 μL of warmed sample buffer [50 mM Tris, 10% (vol/vol) glycerol, 2% SDS, 100 mM DTT, and 0.2 mg/mL bromophenol blue], and boiled (55° C., 15 min). Proteins were resolved on a 4-12% Bis-Tris gradient precast gel (Life Technologies) in Mops-SDS running buffer (Life Technologies) at 200 V constant for ~1 h. 10 μL of the PageRuler Plus Prestained Protein Ladder (10-250 kDa, Thermo Fisher) were loaded alongside the samples. Protein bands were transferred by tank transfer onto a nitrocellulose membrane (3.5 h, 4° C., 30 V constant) in transfer buffer (25 mM Tris pH 8.3, 192 mM glycine, 15% (vol/vol) methanol, and 0.1% SDS). The membranes were blocked with a solution of 5% nonfat milk (BioRad) in tris-buffered saline-tween (TBS-T) (25 mM Tris pH 7.4, 150 mM NaCl, and 0.1% Tween-20) for 1 h at RT and then incubated overnight at 4° C. with primary antibodies (anti-Q1, Alomone) in blocking solution. The blots were washed with TBS-T three times for 10 min each and then incubated with secondary horseradish peroxidase-conjugated antibody for 1 h at RT. After washing in TBS-T, the blots were developed with a chemiluminiscent detection kit (Pierce Technologies) and then visualized on a gel imager. Membranes were then stripped with harsh stripping buffer (2% SDS, 62 mM Tris pH 6.8, 0.8% β-mercaptoethanol) at 50° C. for 30 min, rinsed under running water for 2 min, and washed with TBST (3×, 10 min). Membranes were pretreated with 0.5% glutaraldehyde and reblotted with anti-ubiquitin (VU1, LifeSensors) as per the manufacturers' instructions.

Data and Statistical Analyses

Data were analyzed off-line using FloJo, PulseFit (HEKA), Microsoft Excel, Origin and GraphPad Prism software. Statistical analyses were performed in Origin or GraphPad Prism using built-in functions. Statistically significant differences between means ($P<0.05$) were determined using Student's t test for comparisons between two groups. Data are presented as means±s.e.m.

Example 2

Design, Efficacy and Distinctive Functional Effects of Different Engineered nanoDUBs on Q1

Similar to E3 ligases, some wild-type DUBs have a modular architecture in which the catalytic and substrate targeting domains are separate. To develop nanoDUBs, by following the methods set forth in Example 1, we fused catalytic domains of different DUBs to vhh4 GFP nanobody. We have generated three distinct nanoDUBs—nanoUSP21 (non-selective cleavage of all ubiquitin chain types), nanoOTUD1 (specific for K63 chains), and nanoOTUD4 (specific for K48 chains).

Figure 2:
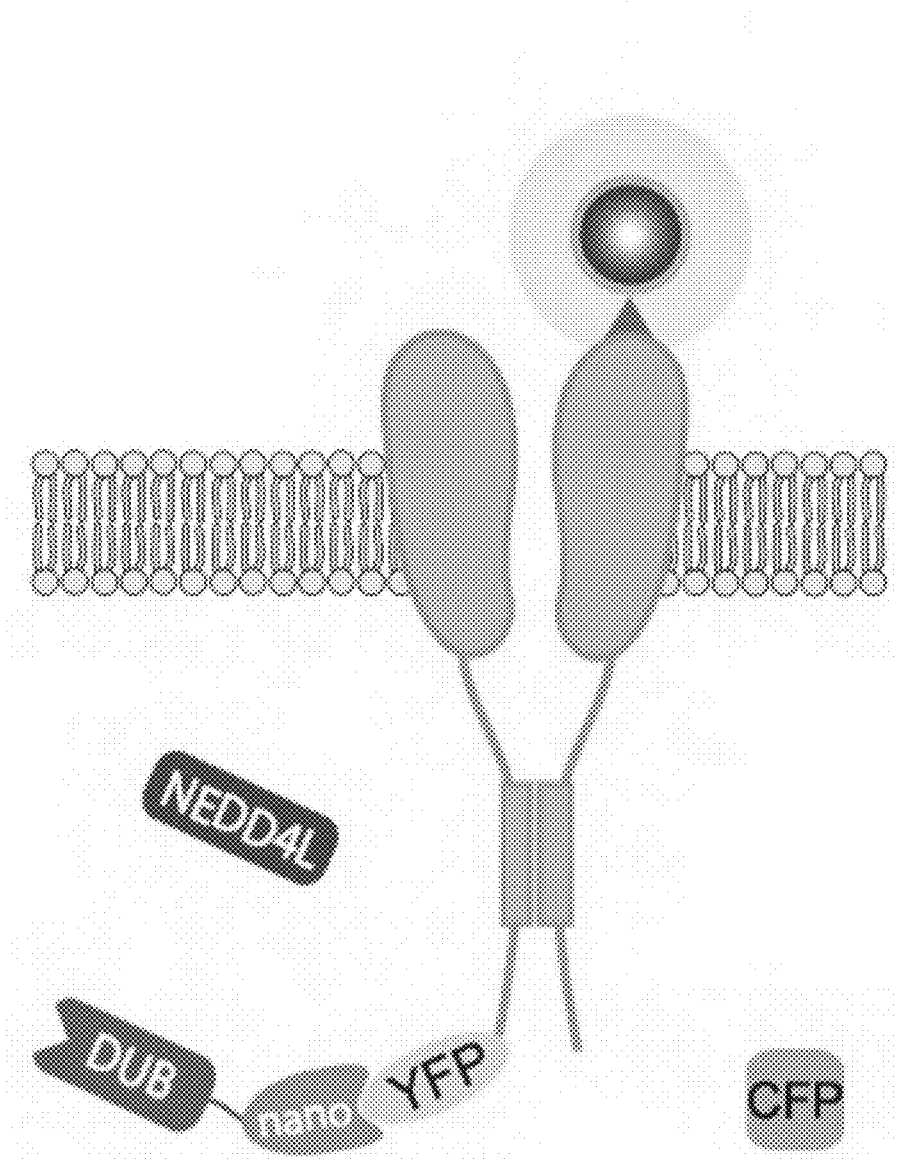
FIG. 2 shows a cartoon of engineered nanoDUBs designed to rescue Nedd4-2 mediated endogenous Q1 ubiquitination and reduction in surface expression.
Figure 3A:
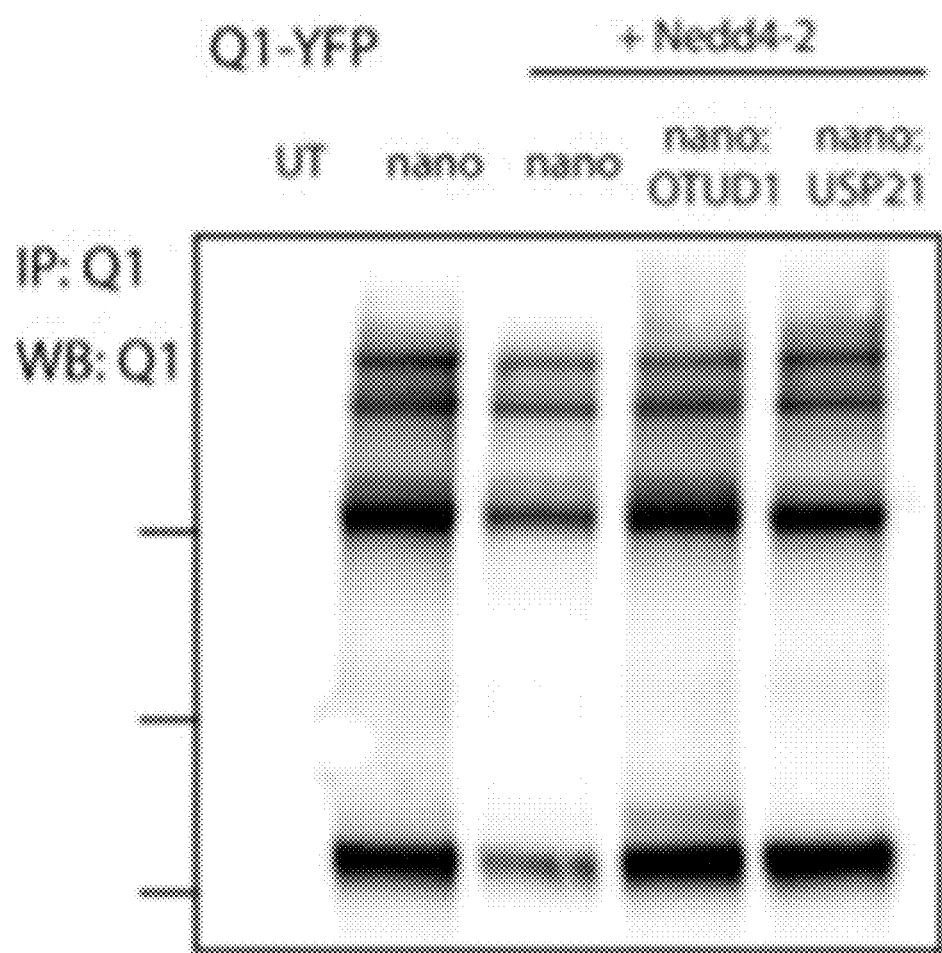
FIGS. 3A and 3B show the impact of nanoDUBs on Nedd4-2-mediated effects on Q1 expression and ubiquitination.
Figure 3B:
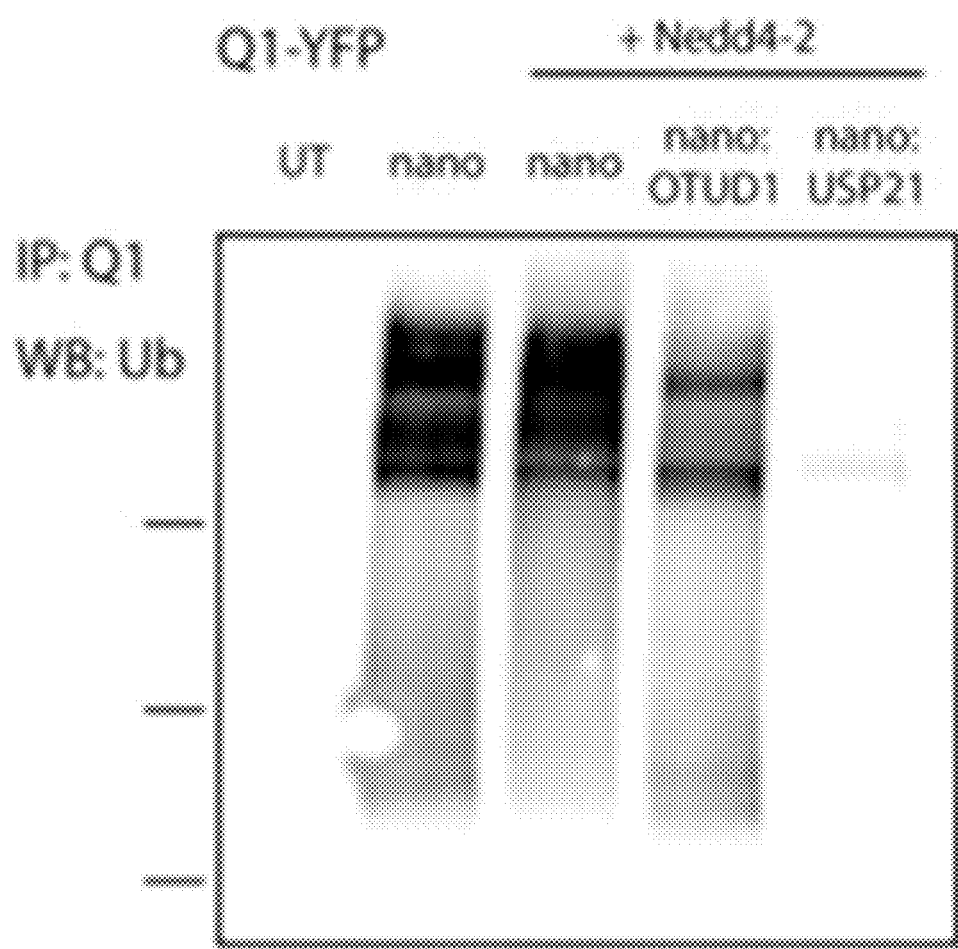

To determine efficacy of the nanoDUBs generated (FIG. 2), we first assessed their ability to reverse Nedd4-2 mediated ubiquitination of Q1-YFP. In pulldown Western blots, co-expression of WT Nedd4-2 led to a significant decrease in Q1-YFP expression compared to control, consistent with a decreased stability of the channel (FIG. 3A). Despite the decreased Q1-YFP protein, the overall level of ubiquitination of the channel was similar between control and Nedd4-2-transfected cells, respectively, indicating a more robust relative channel ubiquitination in the latter group (FIG. 3B). Reassuringly, coexpression with either nanoOTUD1 or nanoUSP21 rescued Q1-YFP expression levels (FIG. 3A) and dramatically reduced ubiquitination of the channel (FIG. 3B). Consistent with the notion that USP21 is a nonselective DUB capable of hydrolyzing all ubiquitin chains, nanoUSP21 erased all ubiquitination of Q1-YFP (FIG. 3B). By contrast, nanoOTUD1 only partially eliminated ubiquitin on Q1-YFP (FIG. 3B), consistent with the idea this nanoDUB only eradicates K63 chains.

Figure 3C:
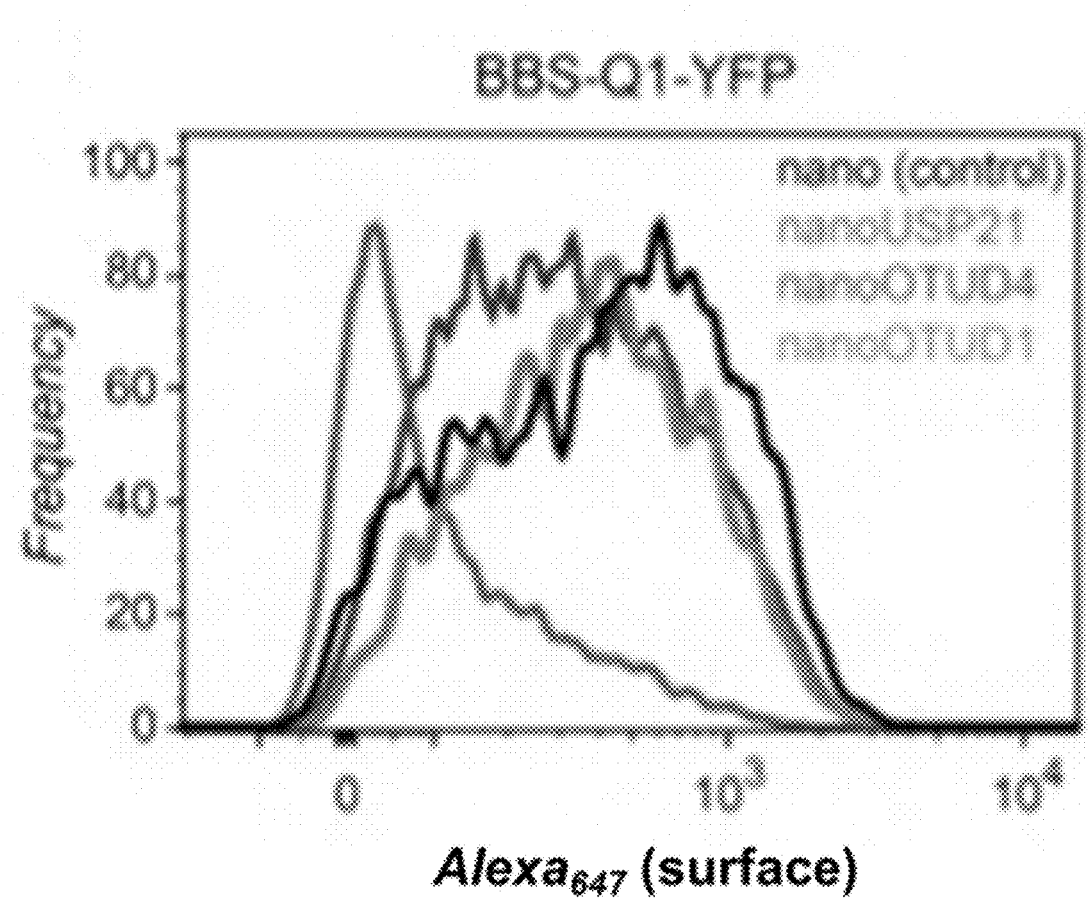
FIGS. 3C and 3D show the impact of nanoDUBs on surface and total Q1 under basal conditions.
Figure 3D:
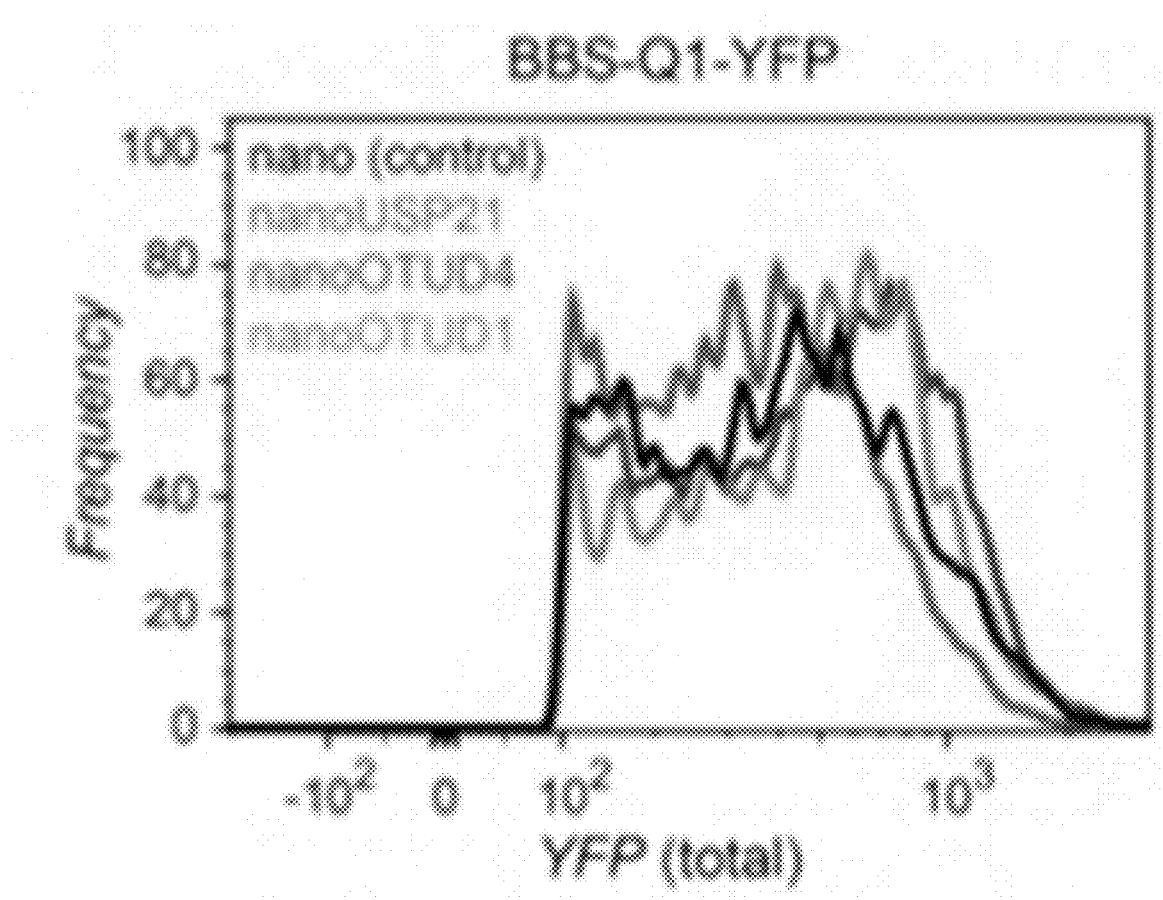

To find out the types of chains presented and their functions as well as potential alterations with co-expression of Nedd4-2, we applied the nanoDUBs in conjunction with our high throughput flow cytometry assays (FIGS. 3C-3F). Co-expressing nanoOTUD1 (eliminates K63) with BBS-Q1-YFP, slightly reduced surface density while slightly increasing total channel expression (FIGS. 3C and 3D; cyan trace). Similarly, nanoUSP21 (eliminates all ubiquitin) modestly decreased surface density (though to a larger extent than nanoOTUD1) and slightly enhanced total channel expression (FIGS. 3C and 3D; green trace). Most surprisingly, OTUD4 (eliminates K48) dramatically decreased channel surface density and modestly decreased total expression (FIGS. 3C and 3D; red trace). These preliminary results suggest a number of far-reaching conclusions that under basal conditions: 1) K48 polyubiquitin chains are important for stabilizing Q1 at the cell surface; 2) ubiquitination is not a major determinant of channel stability (eliminating ubiquitination with nanoUSP21 only slightly increased channel expression; 3) regulation of channel surface density and stability by ubiquitin are discrete events (nanoUSP21 and nanoOTUD1 had opposite effects on the two parameters).

Figure 3E:
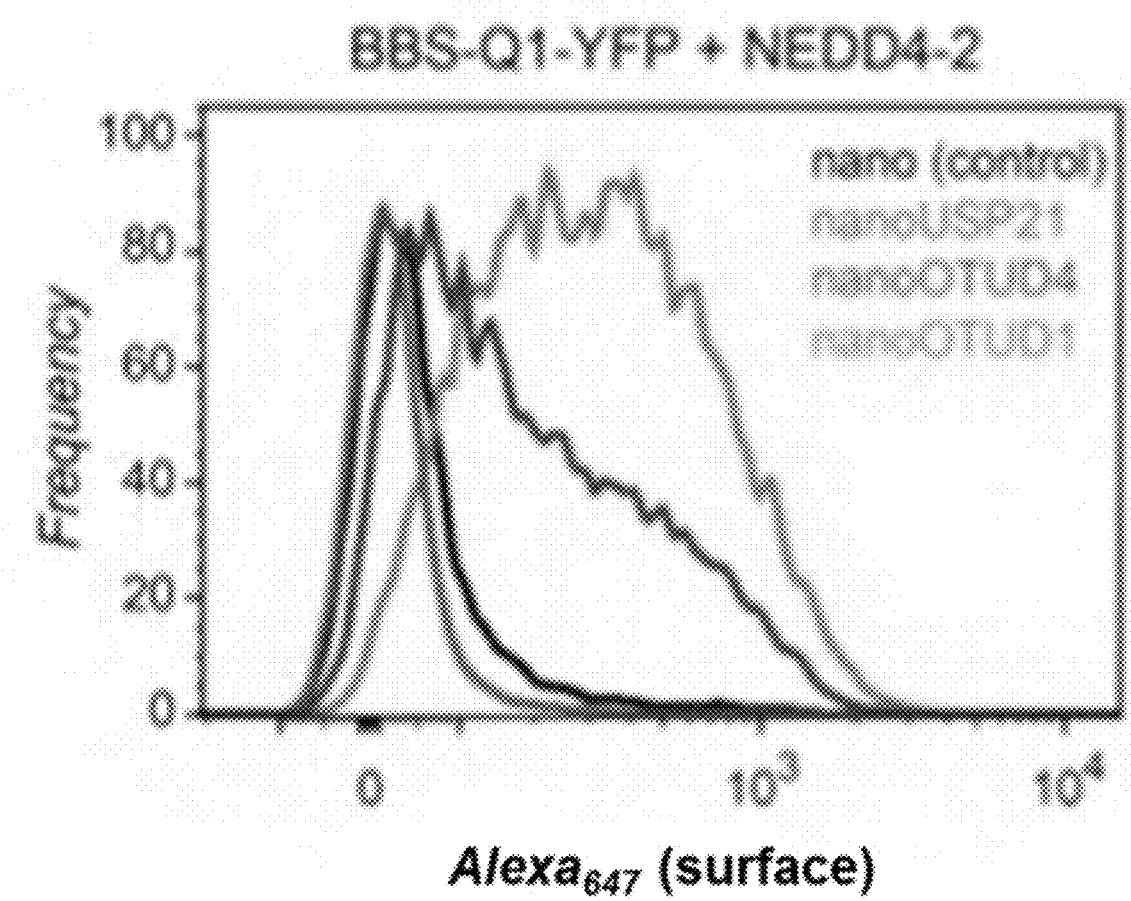
FIGS. 3E and 3F show the impact of nanoDUBs on surface and total Q1 in the presence of Nedd4-2 expression.
Figure 3F:
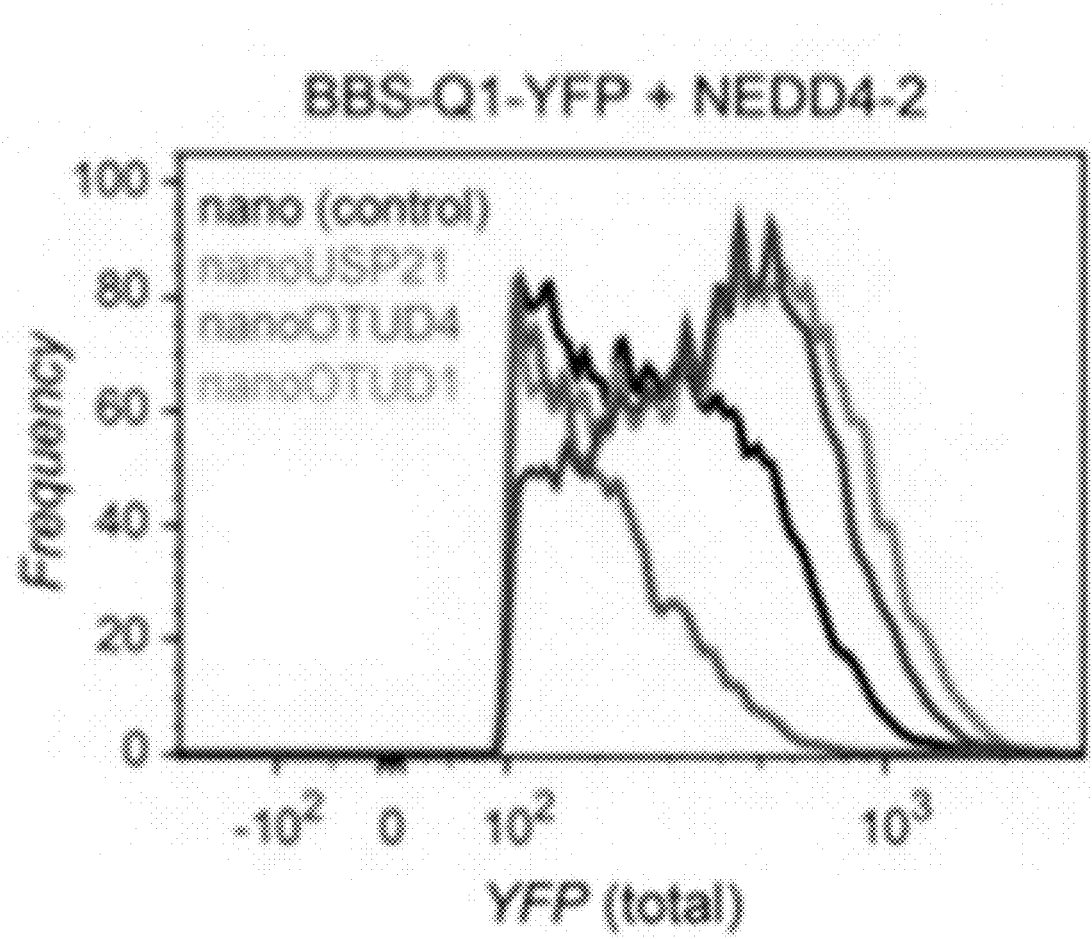

The effects of the nanoDUBs in cells co-expressing BBS-Q1-YFP and Nedd4-2 strengthened these conclusions and offered additional insights (FIGS. 3E and 3F). Under this condition: nanoOTUD1 prevented Nedd4-2-induced marked decrease in channel surface density and total expression (FIGS. 3E and 3F; cyan compared to black traces); nanoOTUD4 further diminished channel surface density and total expression beyond that achieved with Nedd4-2 (FIGS. 3E and 3F; red traces); nanoUSP21 had an intermediate effect on channel surface density (partial rescue) while fully rescuing total expression (FIGS. 3E and 3F; green traces). From these data we can conclude that: 1) Nedd4-2 primarily mediates K63 ubiquitination of Q1 (because Nedd4-2 effects are reversed by OTUD1); 2) K63 chains promote Q1 degradation whereas K48 chains stabilize the channel; 3) K63 chains diminish channel surface density whereas K48 stabilizes channels at the surface.

Example 3

Develop and Validate More nanoDUBs for Distinct Polyubiquitin Chain Types

Beside the nanoDUBs described in Example 2, more nanoDUBs will be designed, including those predicted to be selective for K11 (nanoCezanne), K29/K33 (nanoTRABID), and Met1-linked linear chains (nanoOTULIN).

Western blot approaches with ubiquitin chain-specific antibodies will be used to verify that nanoDUBs are selectively eliminating the specific ubiquitin chains they were designed to target. Experiments will follow the format shown in Example 1. Q1-YFP and HERG-YFP will be co-expressed with individual nanoDUBs±Nedd4-2 in HEK293 and CHO cells. Channels will be pulled down and their expression quantified by Western blots. The blots will then be stripped and probed with ubiquitin chain-specific antibodies. Given the results shown in Example 2, OTUD1 and OTUD4 are expected to selectively eliminate K63 and K48 chains, respectively. The experiments will identify whether the more atypical chains (K6, K11, K29, K33, Met1) contribute to Q1/HERG ubiquitination under basal or Nedd4-2 conditions. If so the same experimental conditions can be used to verify the selectivity of nanoDUBs designed to target these chains. If not, we could increase the representation of these chains by co-expressing specific nanoHECTs. It is expected that these experiments will provide direct evidence that the nanoDUBs act to erase the specific ubiquitin chain types they were designed to target.

Specific nanoDUBs will be deployed in cardiac myocytes to determine whether the functional effects observed in heterologous cells are transferable to the native context.

Example 4

NanoDUBs can Probe the Regulation of Q1 and HERG by Nedd4-Like E3 Ligases

According to the results of Example 2, Nedd4-2 was primarily regulating Q1 via K63 ubiquitin chains. Quite often, however, the precise types of ubiquitin chains conferred by specific E3 ligases on particular substrates and the functions they confer in vivo are unknown, which is the case with several HECT E3 ligases. There are 9 members of the Nedd4-like family of E3 ligases, several of which possess WW motifs that bind PY motifs on substrate proteins. We will systematically compare how co-expression of each of these Nedd4-like E3 ligases affects Q1/HERG channel surface density, total expression, and functional currents. For those that measurably affect any aspect of channel behavior we will co-express them with individual nanoDUBs to gain insights into the ubiquitin chain types they catalyze on the channels to affect their function. Overall, these experiments are expected to provide new insights into how diverse members of the Nedd4-like family of E3 ligases regulate Q1/HERG channels.

Example 5

Develop Inducible nanoDUBs for Spatio-temporal Deubiquitination of Q1 and HERG

To develop an acutely inducible system, the catalytic domains of selected DUBs and vhh4 nanobody will be fused to the rapamycin-binding proteins FRB and FKBP, respectively. The inducible nanoDUB construct (FRB:DUB-P2A-CFP-P2A-FKBP:nano) will be created in three parts. First, FRB:DUB-P2A-CFP will be created by PCR amplifying the DUB catalytic domain and cloning the amplified fragment into FRBxx-P2A-CFP vector using AscI/AflII sites. Second, we will use overlap extension PCR to create a P2A-FKBP: nano cassette which was then cloned downstream of CFP in the FRB:DUB-P2A-CFP construct using BglII/NotI sites, generating FRB:DUB-P2A-CFP-P2A-FKBP-nano.

To add a spatial control to the inducible nanoDUBs, FKBP-nano constructs described above will be modified by adding subcellular targeting motifs (ER—KDEL; Golgi—GalT; plasma membrane—PH domain; endosomes—FYVE motif). Spatio-temporal control of the deubiquitination will enable us to infer whether enzymatic action in a particular subcellular localization is most important to the observed functional effects.

Example 6

NanoDUBs can Decipher Mechanisms and Rescue Low $[K^+]_{o-}$ and Anti-Depressant-Induced Downregulation of HERG Exposure of cells expressing HERG channels to either low extracellular $K^+$ or the anti-depressant desipramine leads to ubiquitin-mediated loss of surface channels that have been attributed to enhanced endocytosis and reduced forward trafficking, respectively. NanoDUBs can be utilized to identify the type of ubiquitination that specifies the two putatively distinct pathways (i.e., endocytosis vs forward trafficking.) HEK293 cells expressing BBS-HERG-YFP±specific nanoDUBs will be exposed to low $[K^+]_o$ (0.2 mM) or 30 μM desipramine for 6 hrs. Flow cytometry will be used to assess the ability of specific nanoDUBs to rescue HERG channel surface density and/or total expression. In addition, Western blots will be used to determine the relative ratios of the immature 135-kDa and fully glycosylated 155-kDa mature form of HERG as a complementary approach to measure channel maturation and trafficking. Possible results may include: 1) specific distinct ubiquitin chain forms specify either arrested forward trafficking or enhanced endocytosis; or alternatively 2) the same type of ubiquitin chain can mediate both effects, which would suggest that the subcellular locale where ubiquitin takes place could be the dominant factor in specifying functional outcomes.

Beyond mechanistic insights, if the low $[K^+]_{o-}$ or desipramine-induced decrease in surface HERG and $I_{Kr}$ can be reversed by nanoDUBs, this would suggest a new druggable target for preventing hypokalemia- and anti-depressant-induced aggravation of LQTS.

Example 7

NanoDUBs Rescue Subset of LQT1 Trafficking-Deficient Mutants

Figure 4A:
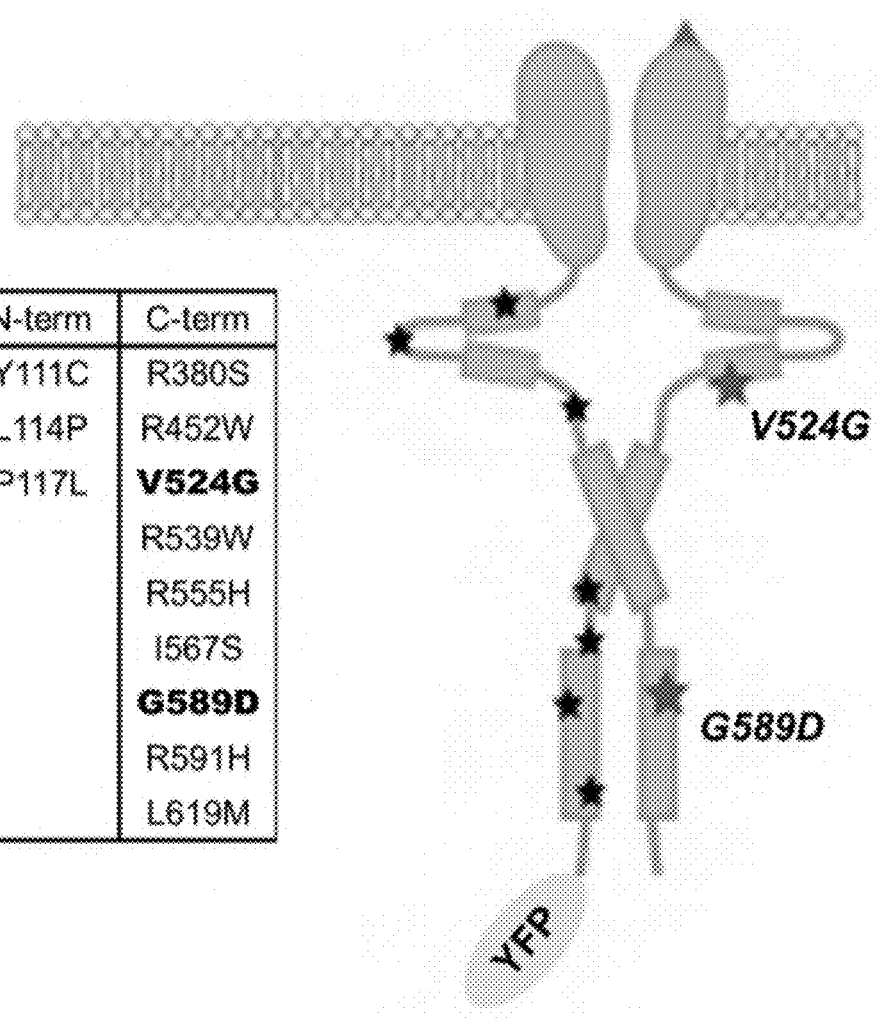
FIG. 4A shows a cartoon of diverse LQT1 mutations.
Figure 4B:
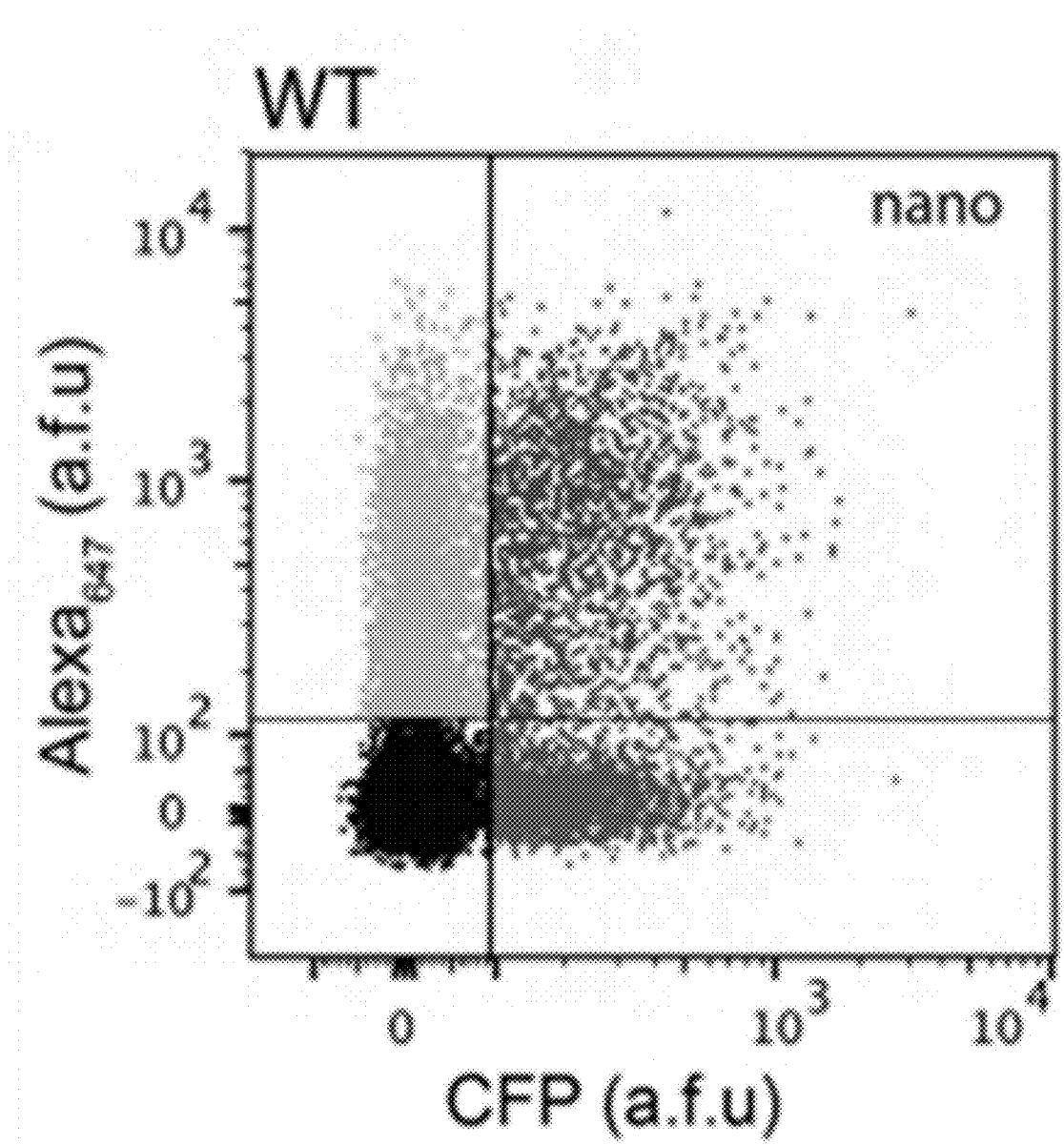
FIG. 4B shows a flow cytometry dot plot graph of WT Q1 surface density.
Figure 4C:
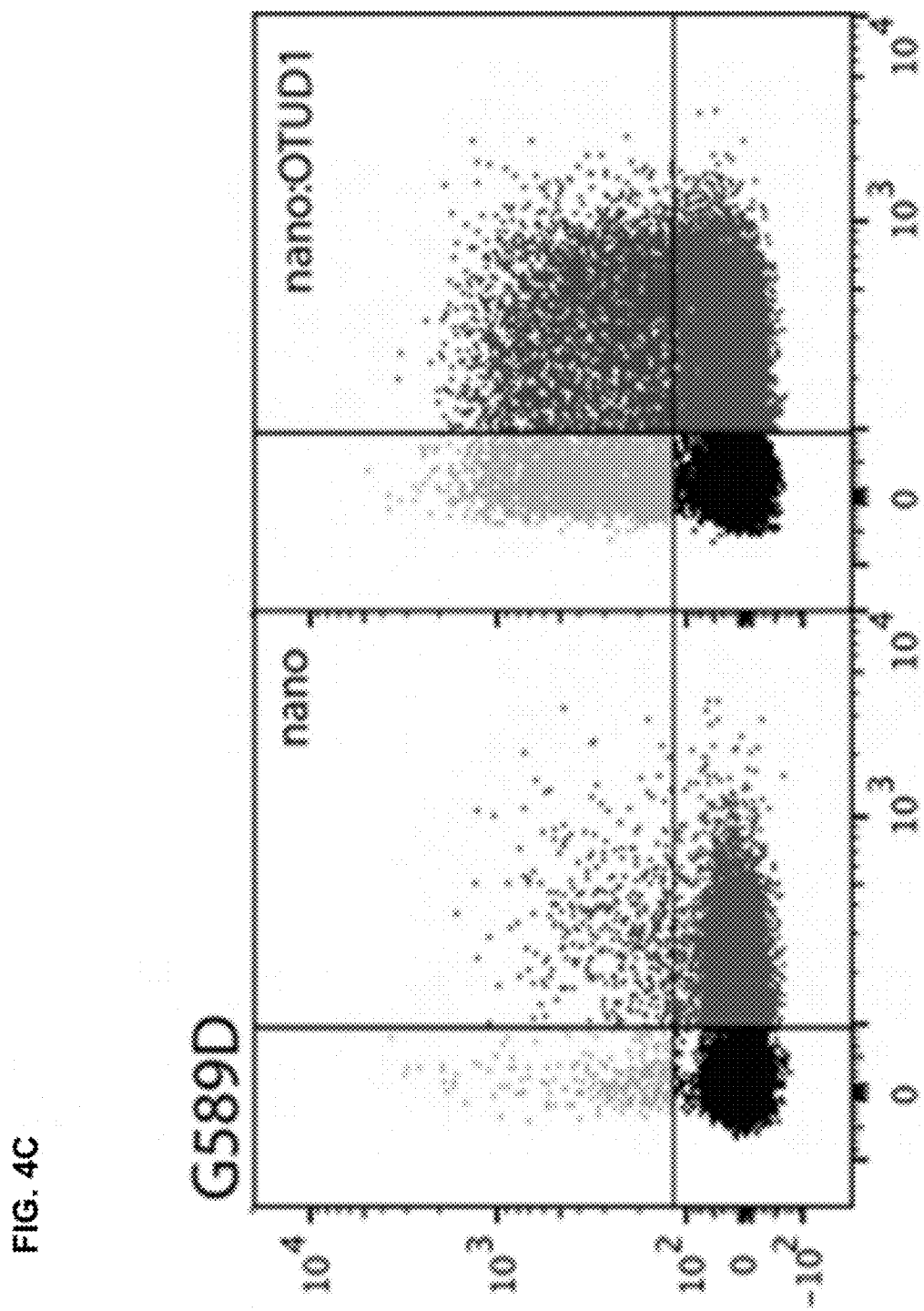
FIGS. 4C and 4D are flow cytometry dot plots showing differential rescue of surface density of two LQT1 mutants (G589D in FIG. 4C, and V524G in FIG. 4D) by nanoOTUD1.
Figure 4D:
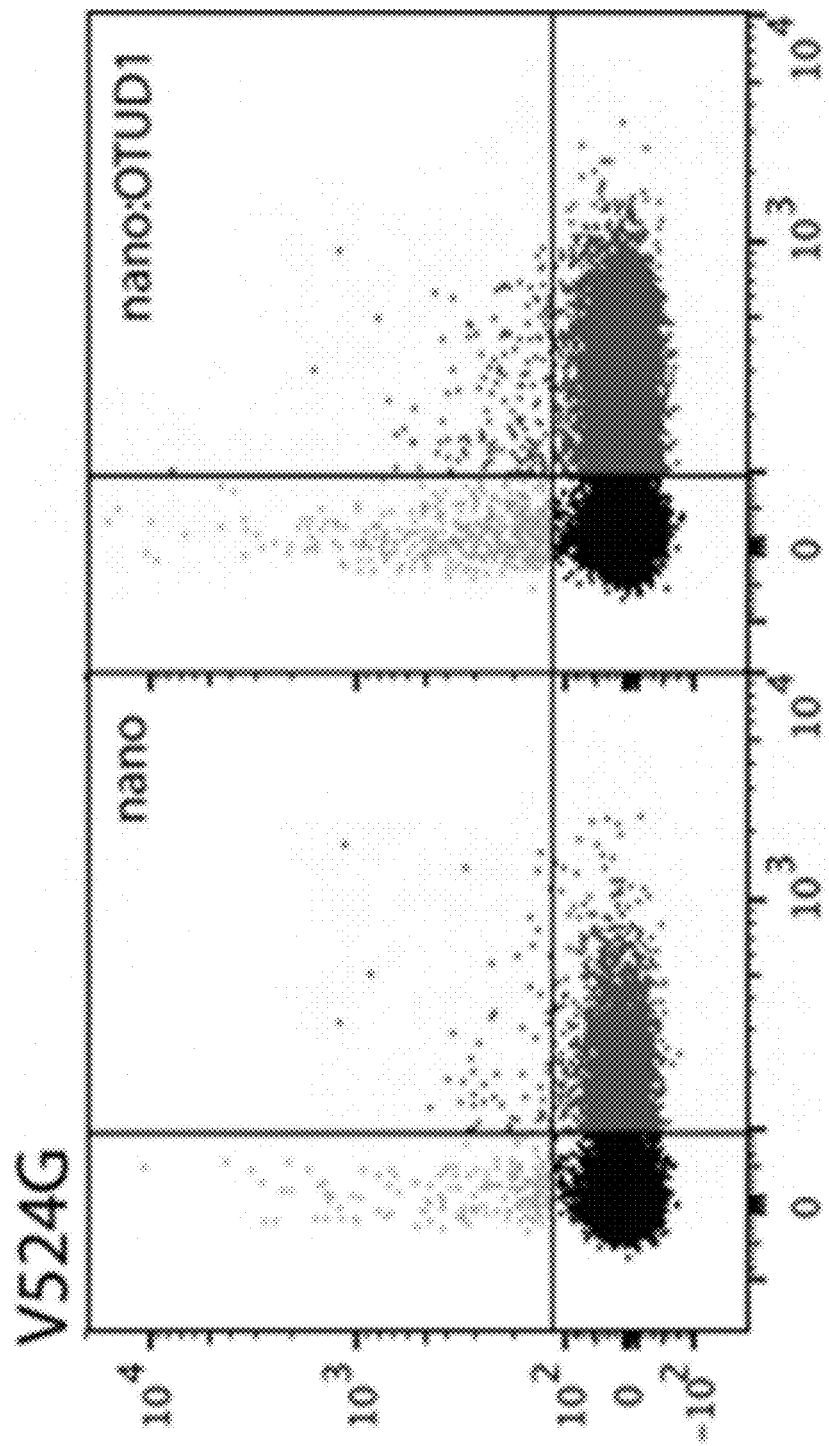

The flow cytometry assay of channel surface density and total expression provides a method to rapidly screen for contributions of trafficking deficiencies to diverse LQT1 mutant channels. This method was previously used to show that homotetrameric Q1 channels containing the G589D LQT1 mutation displayed a strong trafficking deficient phenotype compared to wild-type channels (Aromolaran et al., 2014). This result is reproduced here in the dot plot graph showing reduced density of surface G589D compared to wild-type channels (FIGS. 4B and 4C). Remarkably, co-expressed nanoOTUD1 substantially rescued surface expression of G589D channels (FIG. 4C). By contrast, another trafficking-deficient LQT1 mutation, V524G, was not substantially rescued by nanoOTUD1 (FIG. 4D). These results showed that some trafficking-deficient LQT1 mutations may be correctable by sculpting the particular ubiquitin chains on the channel.

Example 8

NanoDUBs Rescue Subset of LQT2 Trafficking-Deficient Mutants

Figure 5:
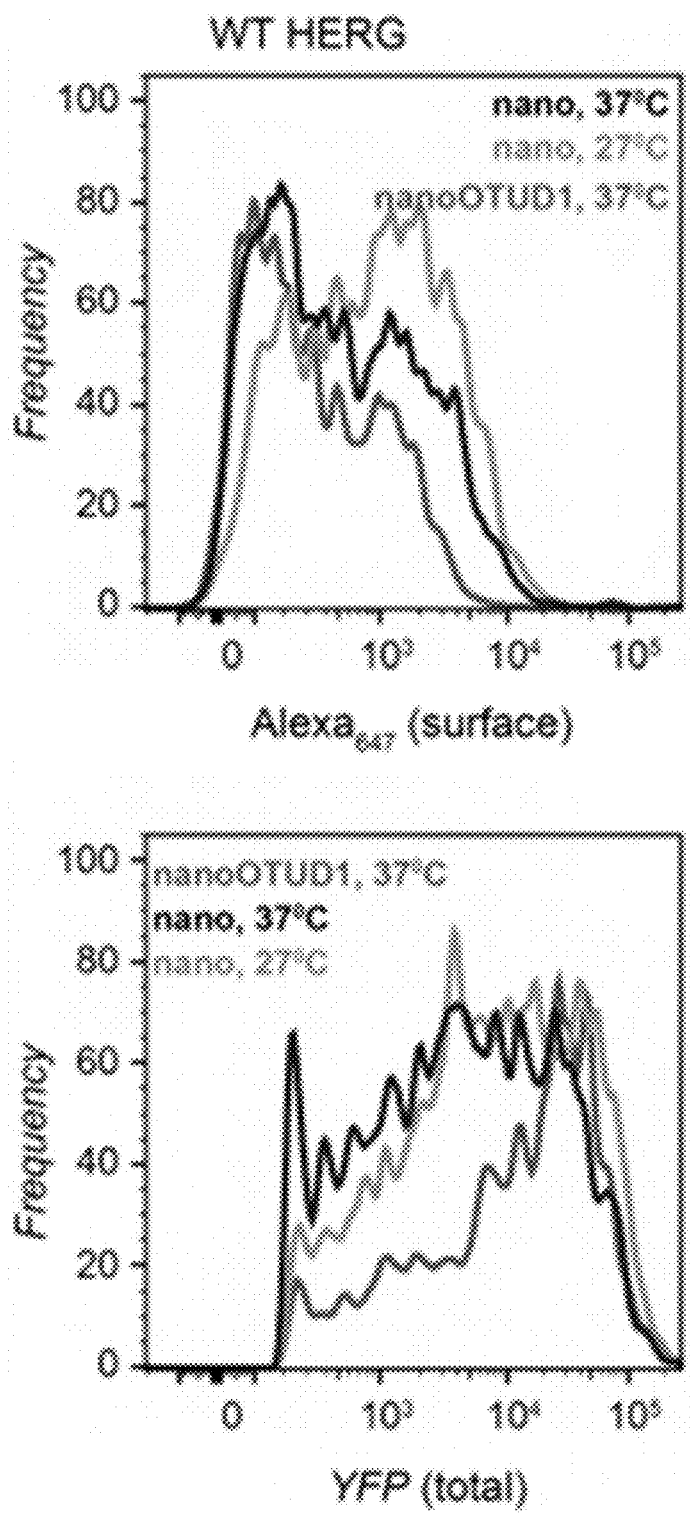
FIG. 5 shows the impact of low temperature and nanoOTUD1 on WT and LQT2 mutant HERG surface (top panel) and total (bottom panel) expression.
Figure 5:
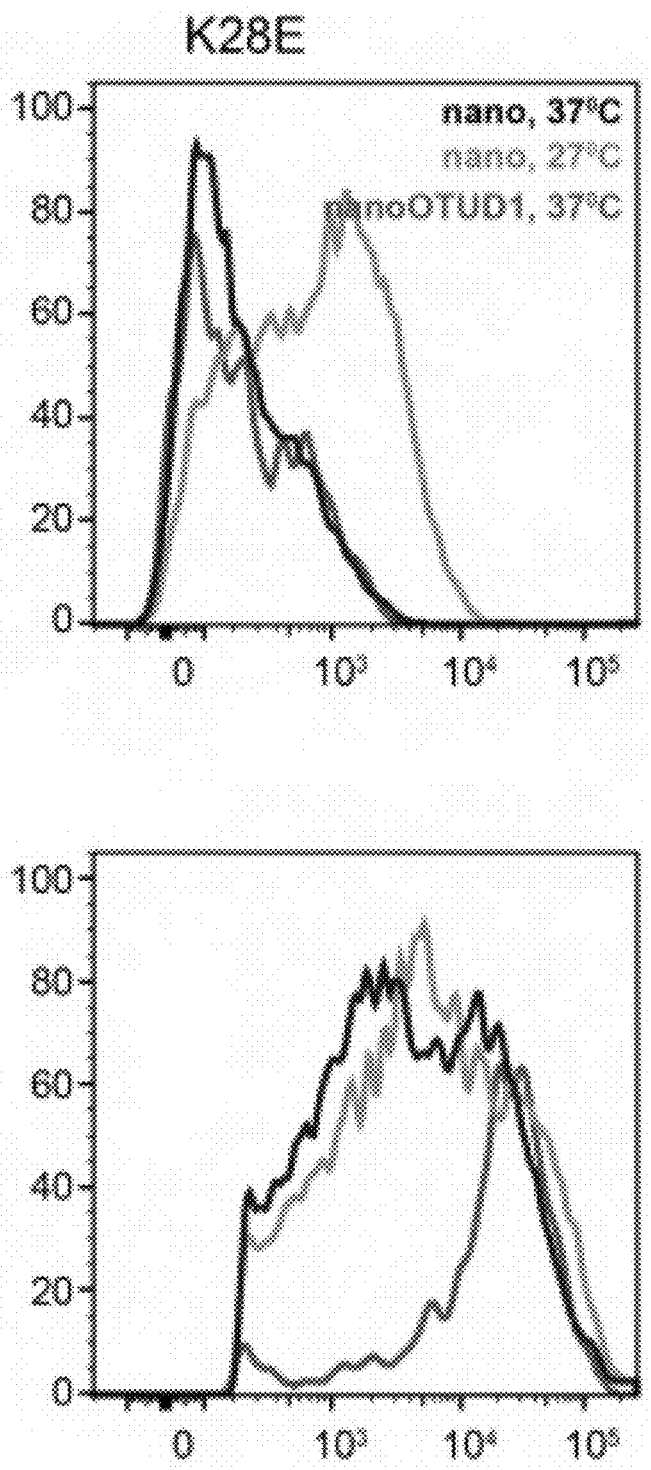
Figure 5:
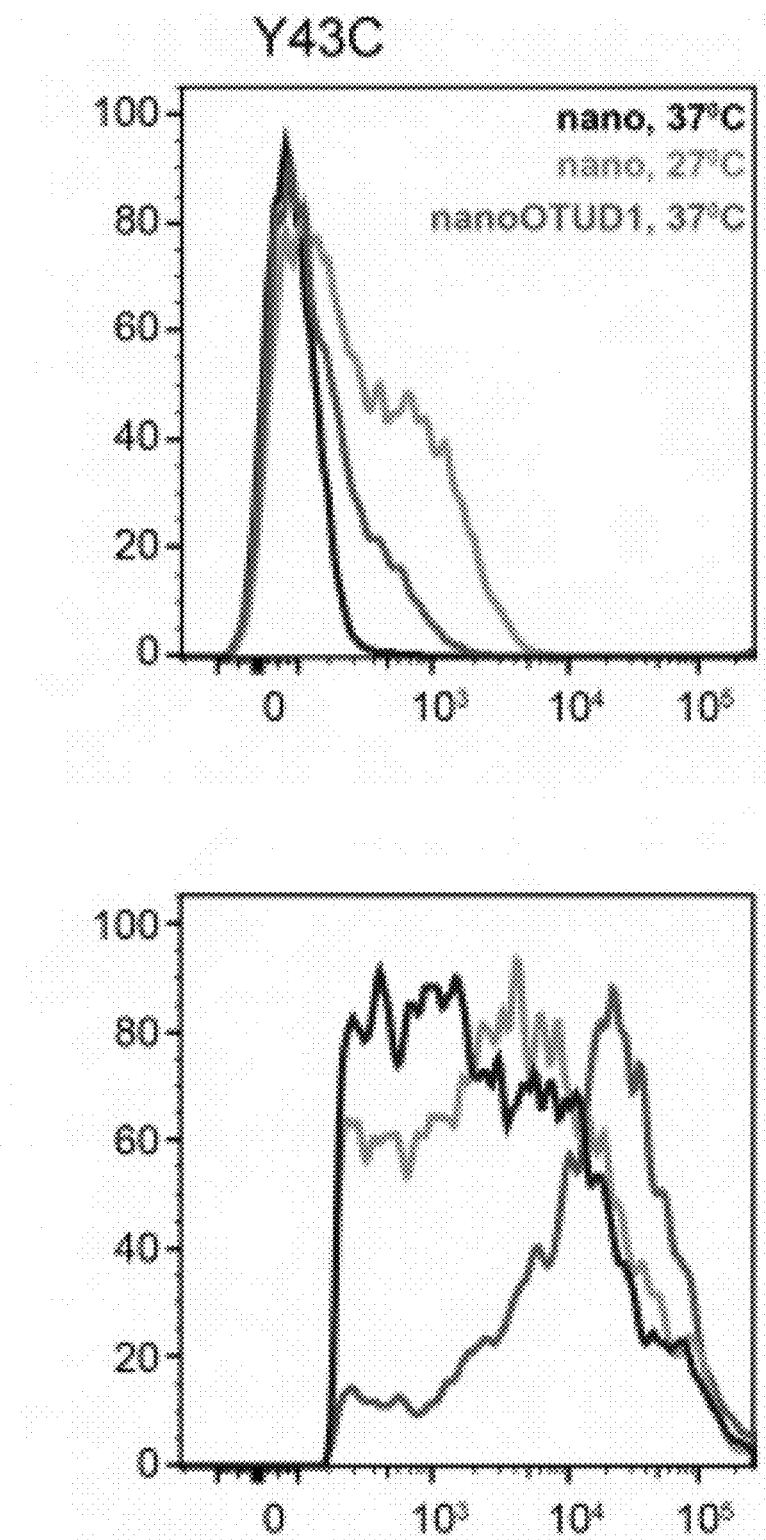
Figure 5:
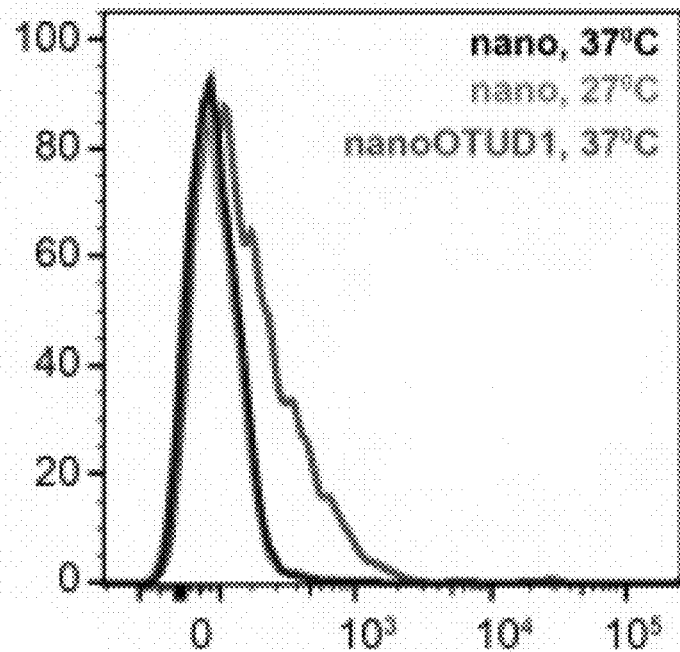
Figure 5:
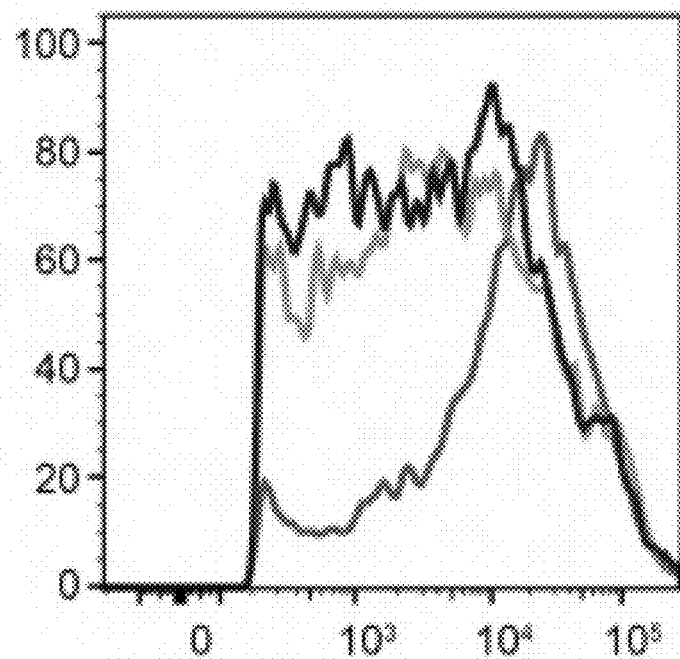
Figure 6A:
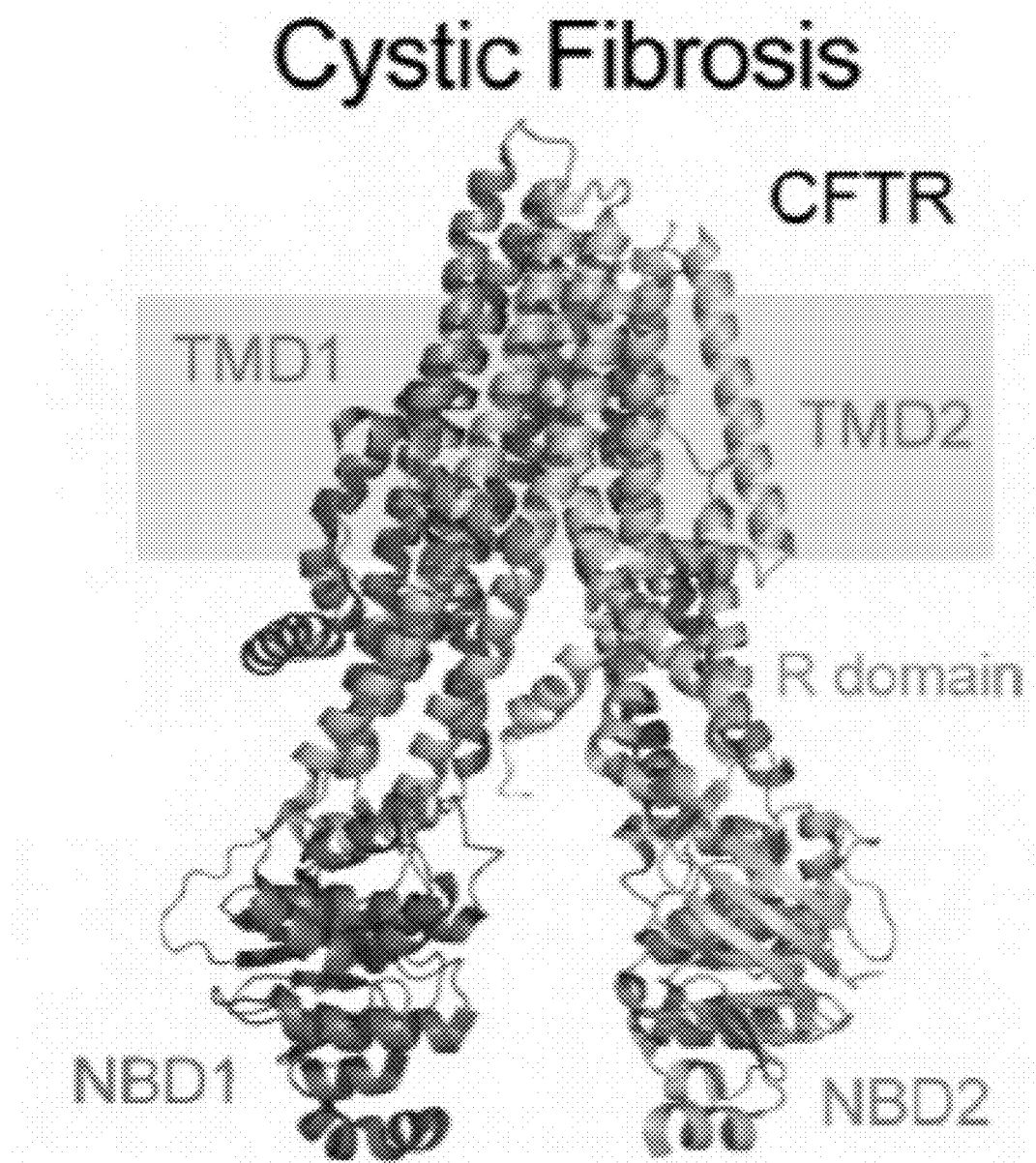
FIGS. 6A-6G show that CF-targeted enDUBs functionally rescue common and rare trafficking-deficient CFTR mutations in novel combination therapy.
Figure 6B:
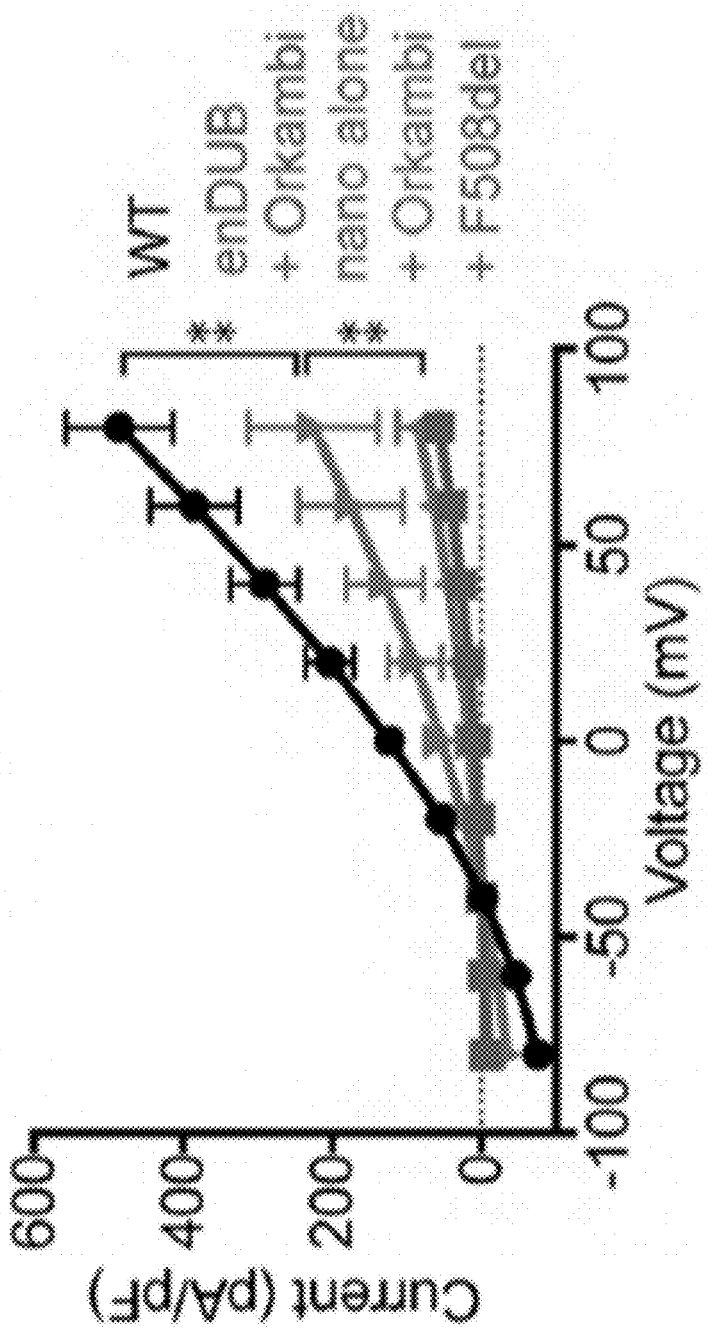
Figure 6C:
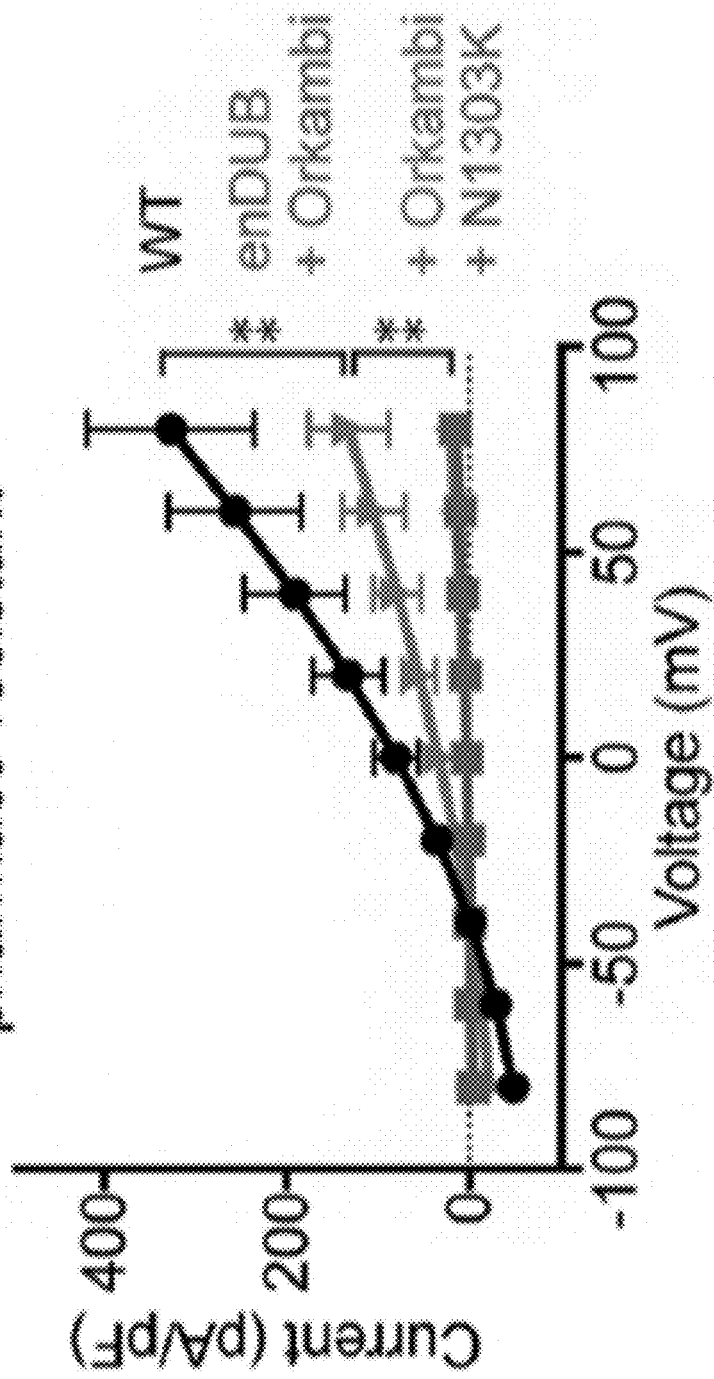
Figure 6D:
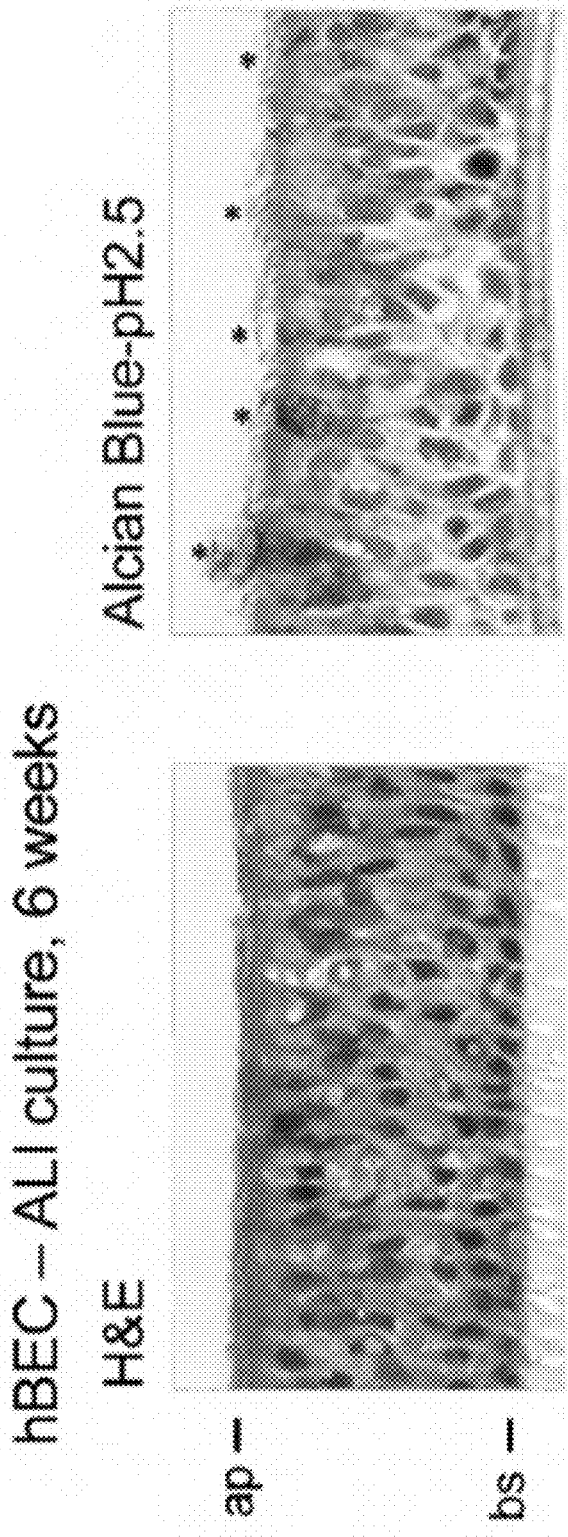
Figure 6E:
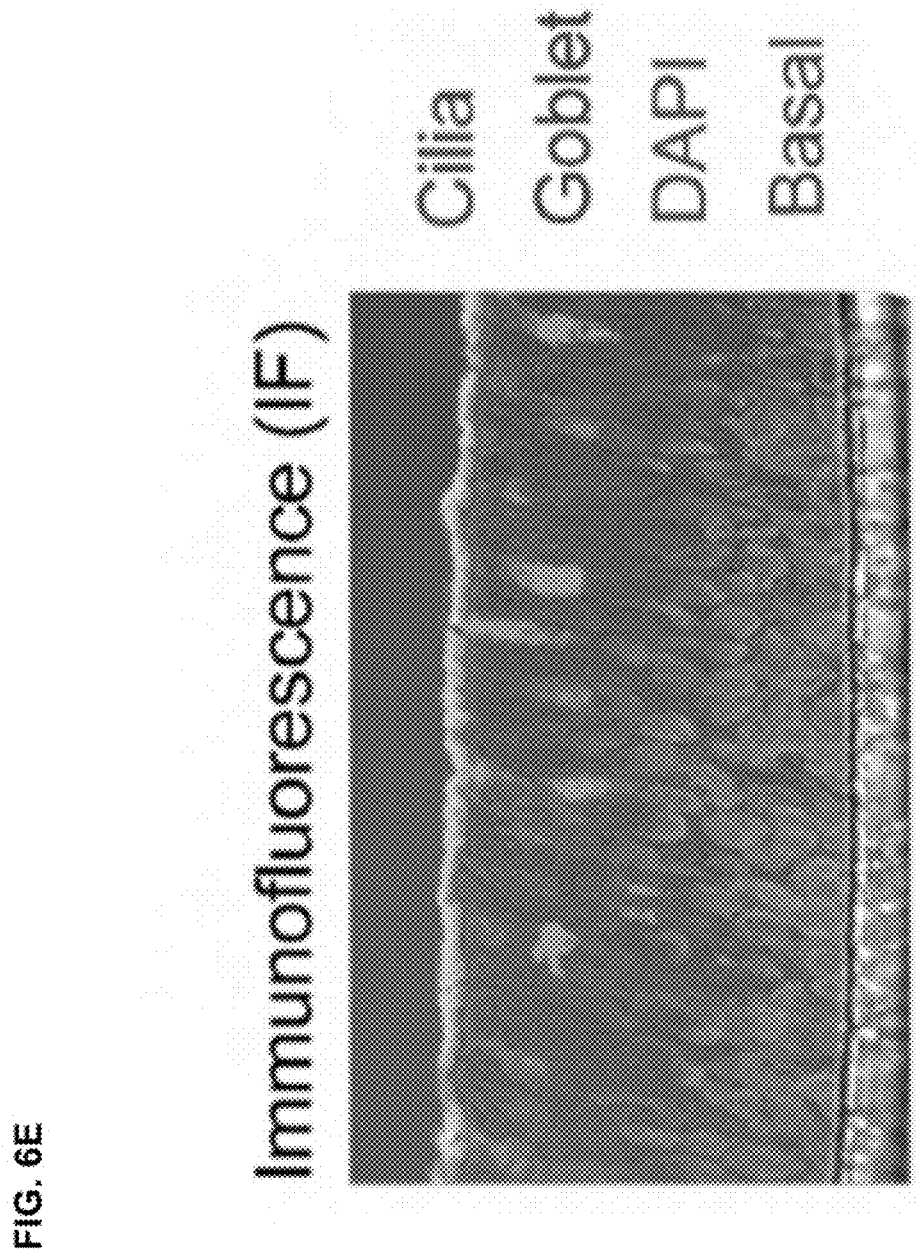
Figure 6F:
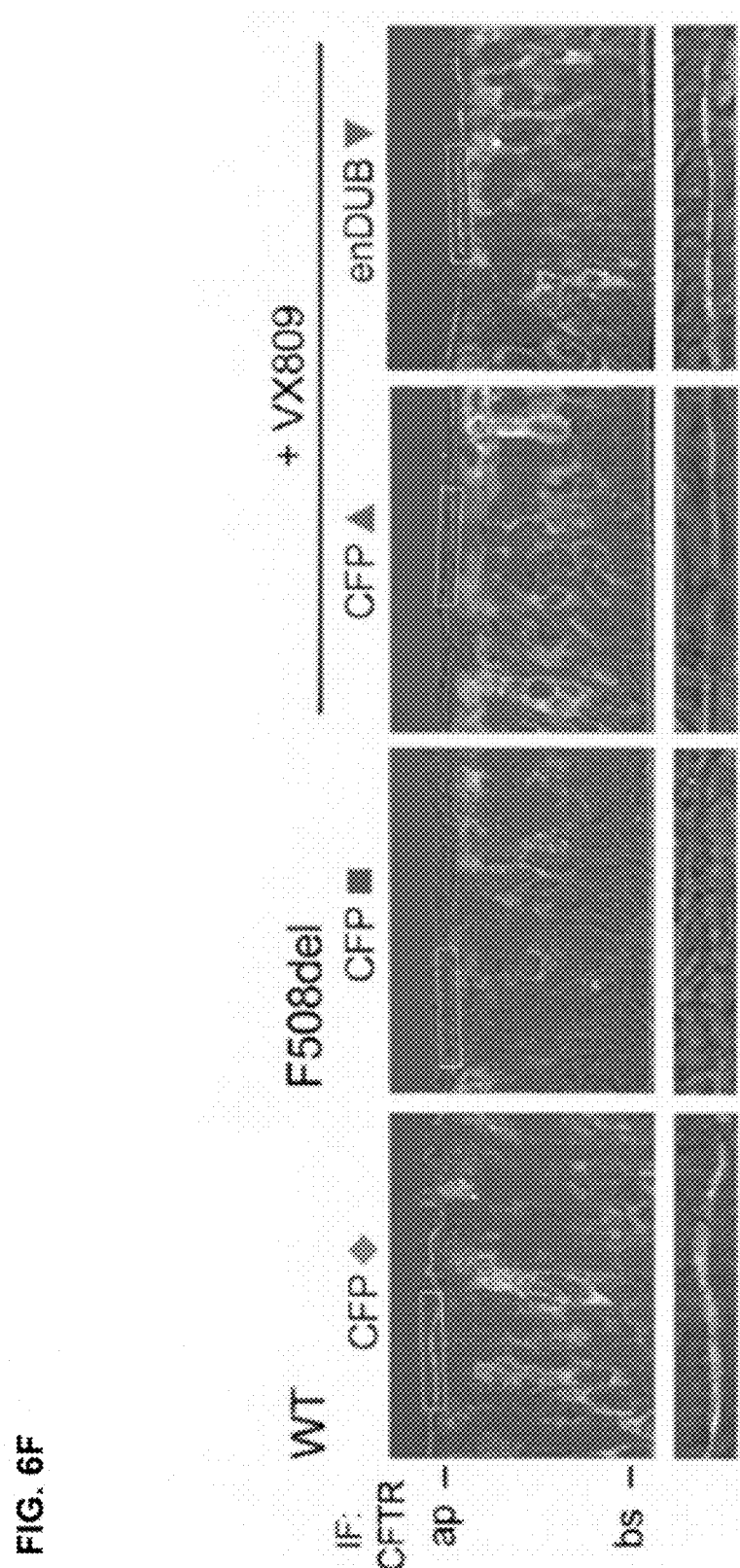
Figure 6G:
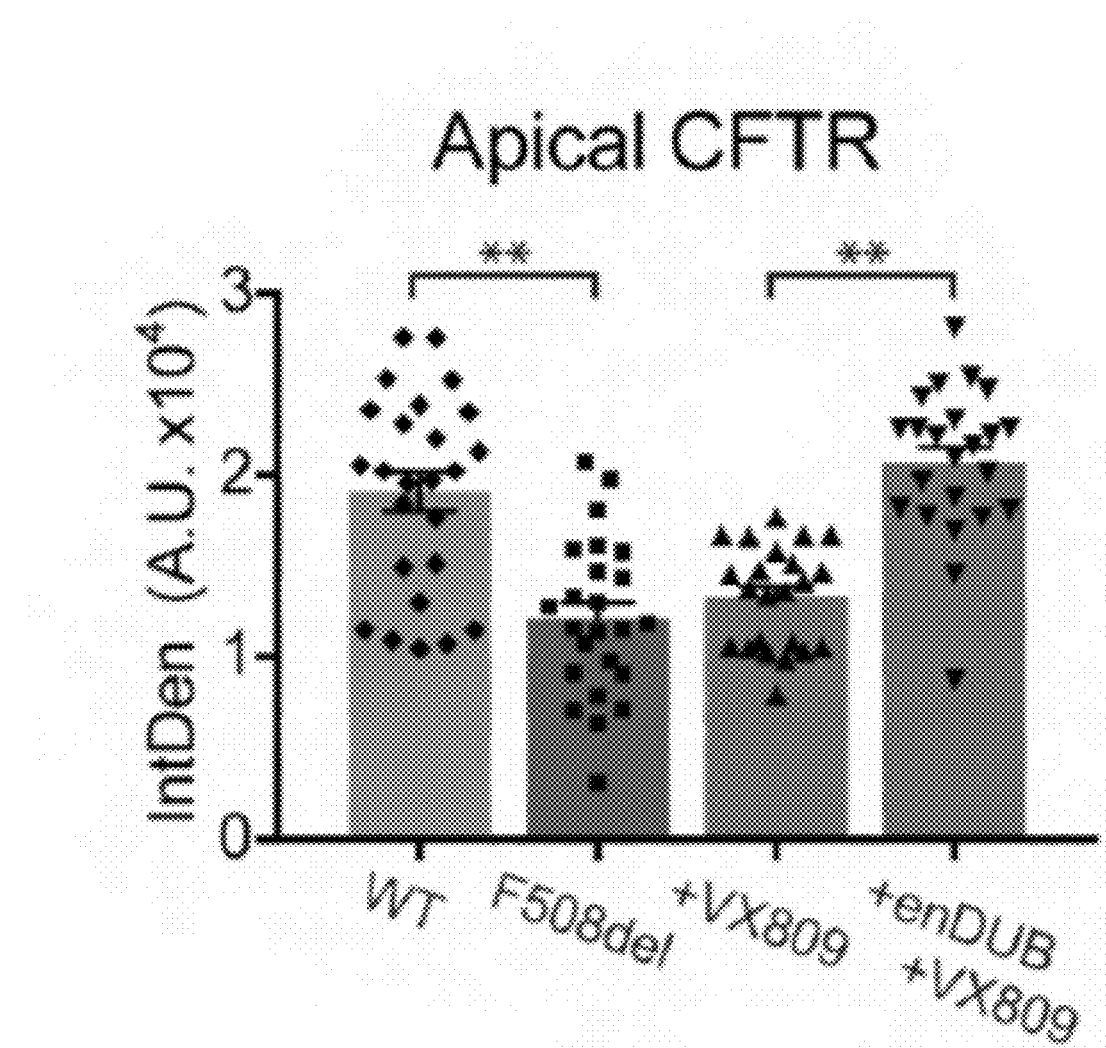
Figure 7A:
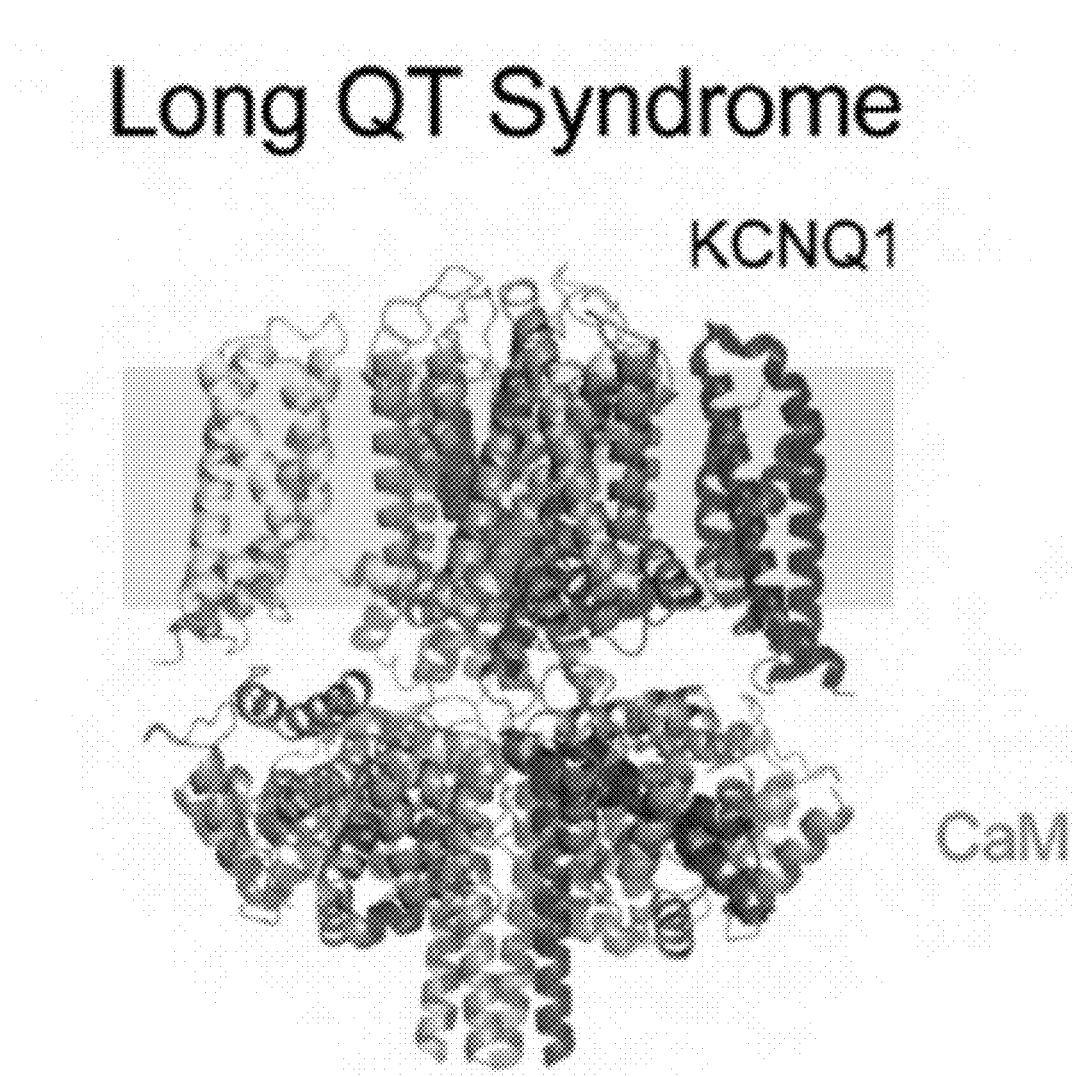
FIGS. 7A-7D show that enDUBs rescue trafficking-deficient KCNQ1 mutations underlying Long QT Syndrome (LQTS) type 1.
Figure 7B:
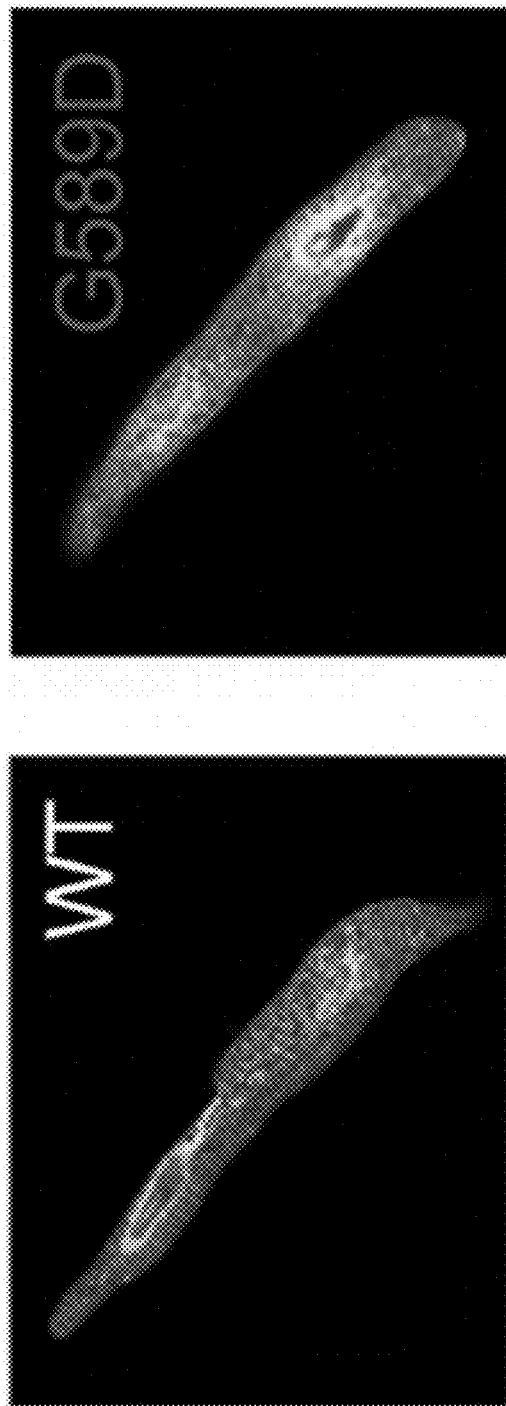
Figure 7C:
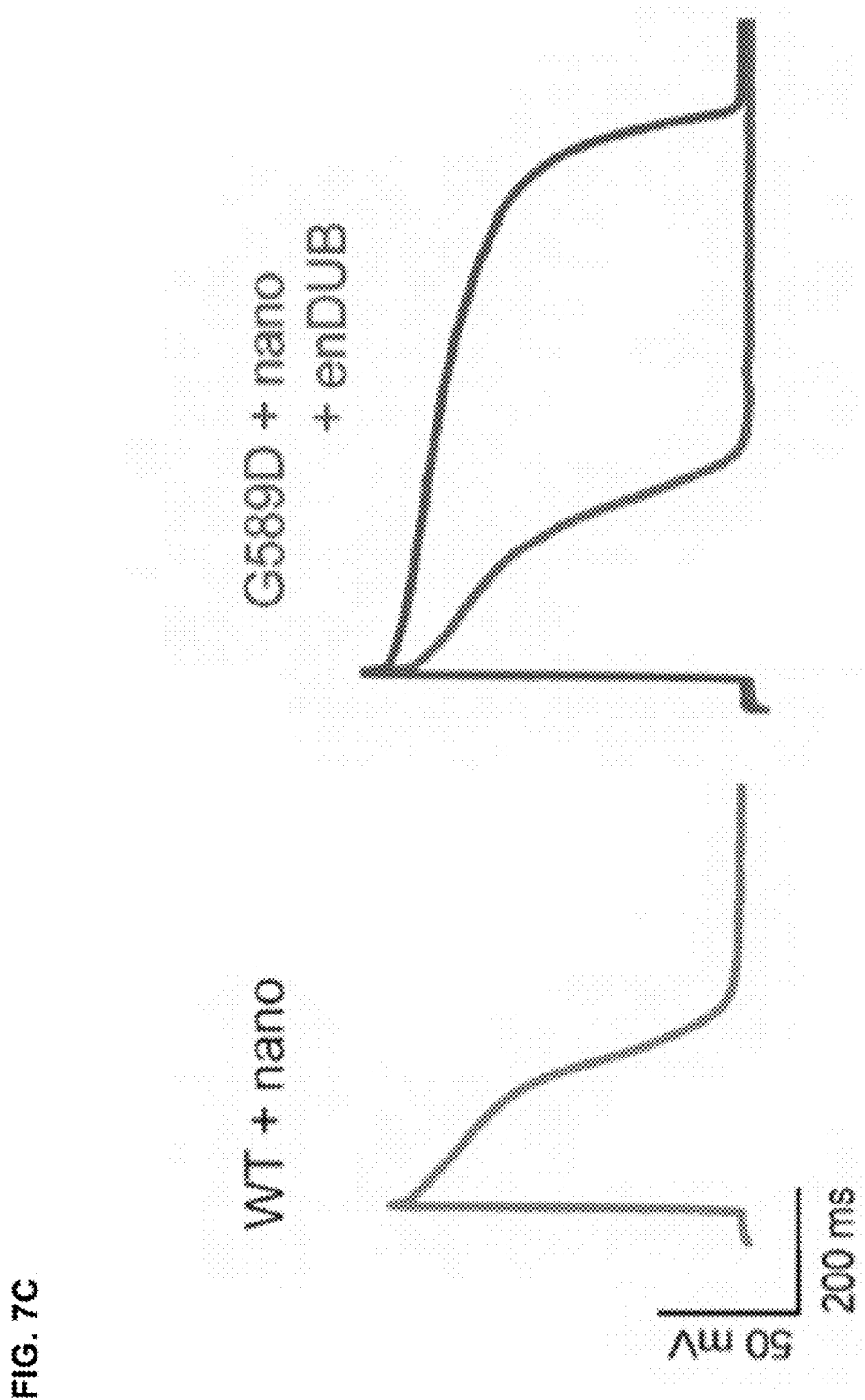
Figure 7D:
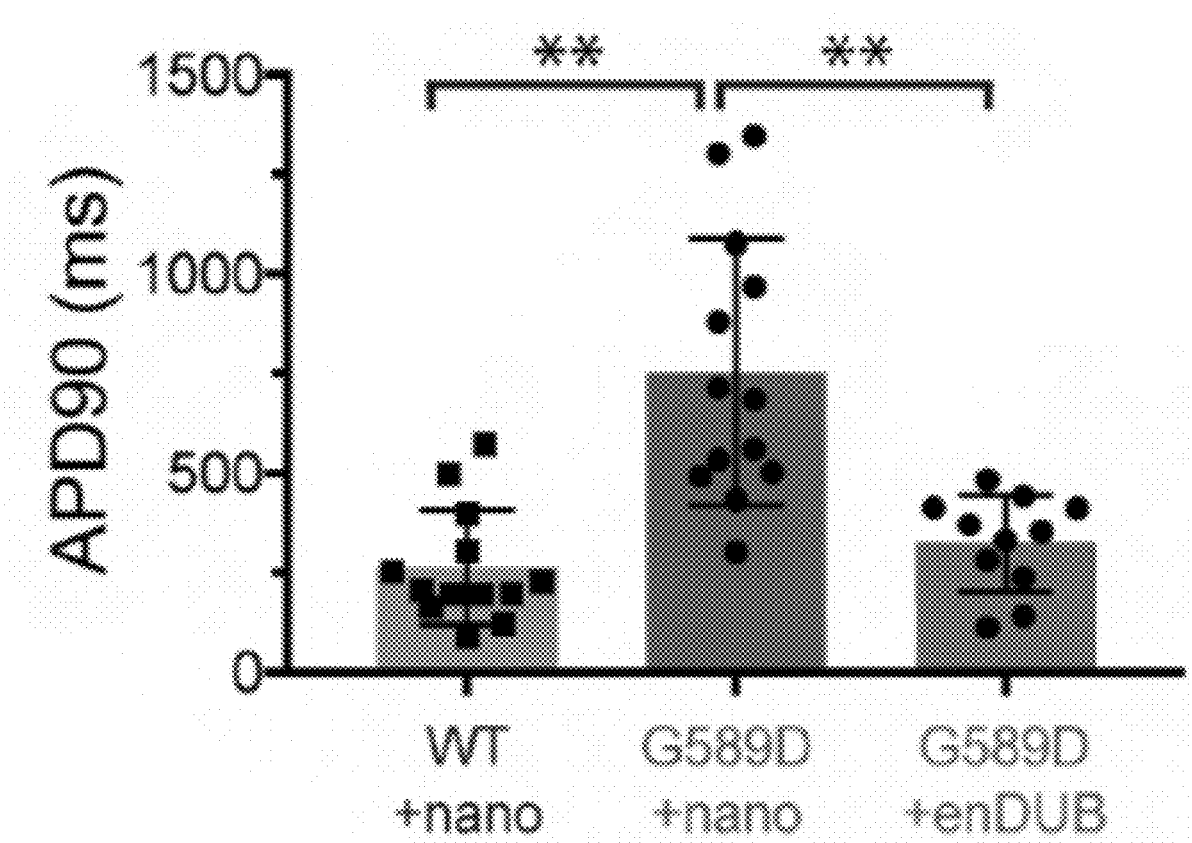

The flow cytometry approach was also utilized to assess trafficking-deficient LQT2 mutants, and some of these mutants were shown to be rescued by modulating the ubiquitin status of the channel. A comprehensive analysis was conducted on 167 LQT2-linked missense mutations. FIG. 5 shows data from three LQT2 mutations from that study, two of which (K28E and Y43C) were found to be correctable by incubating cells at 27° C., and the other, C44F, uncorrectable by either low temperature or with the pore-blocker E-4031. The flow cytometry method showed that all three mutants diminished surface density of HERG, as indicated by leftward shifts in the histograms (FIG. 5, top; black traces) compared to wild-type channels. Culturing cells at 27° C. resulted in rescue of HERG surface expression in K28E and Y43C (FIG. 5, top; rightward shifts in cyan compared to black traces), but not C44F mutants, in agreement with the previous study. Excitingly, nanoOTUD1 also rescued some surface expression of Y43C and C44F (but not K28E) channels at 37° C. Beyond surface density, our approach also indicated Y43C diminished stability of the channel (FIG. 5, bottom), and that nanoOTUD1 increased stability of the channel in all cases (FIG. 5, bottom; right-shifted red traces). Overall, these results validated the use of the flow cytometry approach for these studies. Moreover, the success of this initial foray provided strong motivation to further probe the putative role of aberrant ubiquitination across diverse LQT2 missense mutations and investigating which subset can be rescued by modifying the ubiquitin status of HERG.

Example 9

Screen Diverse LQT1 and LQT2 Missense Mutations to Discover the Subset of Trafficking-Deficient Mutants that can be Rescued by NanoDUBs The flow cytometry approach employed in Example 1 will be used to screen all identified LQT1/LQT2 mutations. Start with expressing 50 LQT1 and 50 LQT2 mutations that are randomly picked from a pool of disease-causing mutations distributed across different regions of the respective channels. For each mutation, quantify the following: the severity of the trafficking deficiency (e.g., mean Alexa647 intensity compared to WT channels), the impact on total expression (e.g., mean YFP signal compared to WT channels), and the impact of nanoOTUD1 on these parameters (by co-expressing the mutation and nanoOTUD1).

To identify particular mutations that alter the ubiquitination status in either the extent and/or phenotype of ubiquitin chanins of the channel, use ubiquitin chain-specific antibodies to determine the change of ubiquitin status of Q1/HERG by these mutations. For those mutations result in a relative increase in K63 chains on the channel, further express them in cardiomyocytes to confirm that a similar change occurs in the native context. Mass spectrometry is also used.

Electrophysiological analyses will be conducted on those mutant that can be "corrected" by the co-expression with nanoOTUD1. First, confirm whether corrected mutant channels express $I_{Ks}$ and $I_{Kr}$ currents. Mutant channels will be expressed under the conditions identified from the above experiments to result in the greatest rescue of surface channels. Then, compare current amplitude and key parameters ($V_{0.5}$ of activation, kinetics of activation and deactivation) between corrected and wild-type channels. Assessment will be conducted in both homotetrameric and heterotetrameric channels featuring co-expressed mutant and wild-type channels, to mimic the autosomal dominant nature of most LQT1/LQT2 conditions.

All patents, patent applications, and publications cited herein are incorporated herein by reference in their entirety as if recited in full herein.

The disclosure being thus described, it will be obvious that the same may be varied in many ways. Such variations are not to be regarded as a departure from the spirit and scope of the disclosure and all such modifications are intended to be included within the scope of the following claims.

CITED DOCUMENTS

1. Moss, A. J. & Kass, R. S. Long QT syndrome: from channels to cardiac arrhythmias. *J Clin Invest* 115, 2018-2024, doi:10.1172/JCI25537 (2005).
2. Shimizu, W. The long QT syndrome: therapeutic implications of a genetic diagnosis. *Cardiovasc Res* 67, 347-356, doi:S0008-6363(05)00164-1 [pii]10.1016/j.cardiores.2005.03.020 (2005).
3. Tester, D. J., Will, M. L., Haglund, C. M. & Ackerman, M. J. Compendium of cardiac channel mutations in 541 consecutive unrelated patients referred for long QT syndrome genetic testing. *Heart Rhythm* 2, 507-517, doi: S1547-5271(05)00191-8 [pii]10.1016/j.hrthm.2005.01.020 (2005).
4. Barhanin, J. et al. K(V)LQT1 and IsK (minK) proteins associate to form the I(Ks) cardiac potassium current. *Nature* 384, 78-80, doi:10.1038/384078a0 (1996).
5. Sanguinetti, M. C. et al. Coassembly of K(V)LQT1 and minK (IsK) proteins to form cardiac I(Ks) potassium channel. *Nature* 384, 80-83, doi:10.1038/384080a0 (1996).
6. Abbott, G. W. et al. MiRP1 forms IKr potassium channels with HERG and is associated with cardiac arrhythmia. *Cell* 97, 175-187, doi:S0092-8674(00)80728-X [pii] (1999).
7. Curran, M. E. et al. A molecular basis for cardiac arrhythmia: HERG mutations cause long QT syndrome. *Cell* 80, 795-803 (1995).
8. Grilo, L. S., Carrupt, P. A. & Abriel, H. Stereoselective Inhibition of the hERG1 Potassium Channel. *Front Pharmacol* 1, 137, doi:10.3389/fphar.2010.00137 (2010).
9. George, A. L., Jr. Molecular and genetic basis of sudden cardiac death. *J Clin Invest* 123, 75-83, doi:62928 [pii] 10.1172/JCI62928 (2013).
10. Tester, D. J. & Ackerman, M. J. Cardiomyopathic and channelopathic causes of sudden unexplained death in infants and children. *Annu Rev Med* 60, 69-84, doi: 10.1146/annurev.med.60.052907.103838 (2009).

11. Peroz, D. et al. Kv7.1 (KCNQ1) properties and channelopathies. *J Physiol* 586, 1785-1789, doi:10.1113/jphysiol.2007.148254 (2008).

12. Anderson, C. L. et al. Large-scale mutational analysis of Kv11.1 reveals molecular insights into type 2 long QT syndrome. *Nat Commun* 5, 5535, doi:10.1038/ncomms6535 (2014).

13. Aromolaran, A. S., Subramanyam, P., Chang, D. D., Kobertz, W. R. & Colecraft, H. M. LQT1 mutations KCNQ1 C-terminus assembly domain suppress IKs using different mechanisms. *Cardiovasc Res* 104, 501-511, doi:10.1093/cvr/cvu231 (2014).

14. Kanki, H., Kupershmidt, S., Yang, T., Wells, S. & Roden, D. M. A structural requirement for processing the cardiac K+ channel KCNQ1. *J Biol Chem* 279, 33976-33983, doi:10.1074/jbc.M404539200 [pii] (2004).

15. Wiener, R. et al. The KCNQ1 (Kv7.1) COOH terminus, a multitiered scaffold for subunit assembly and protein interaction. *J Biol Chem* 283, 5815-5830, doi:10.1074/jbc.M707541200 [pii] (2008).

16. Hershko, A. & Ciechanover, A. The ubiquitin system. *Annu Rev Biochem* 67, 425-479, doi:10.1146/annurev.biochem.67.1.425 (1998).

17. Komander, D. The emerging complexity of protein ubiquitination. *Biochem Soc Trans* 37, 937-953, doi:10.1042/BST0370937 (2009).

18. Heride, C., Urbe, S. & Clague, M. J. Ubiquitin code assembly and disassembly. *Curr Biol* 24, R215-220, doi:10.1016/j.cub.2014.02.002 (2014).

19. Foot, N., Henshall, T. & Kumar, S. Ubiquitination and the Regulation of Membrane Proteins. *Physiol Rev* 97, 253-281, doi:10.1152/physrev.00012.2016 (2017).

20. MacGurn, J. A., Hsu, P. C. & Emr, S. D. Ubiquitin and membrane protein turnover: from cradle to grave. *Annu Rev Biochem* 81, 231-259, doi:10.1146/annurev-biochem-060210-093619 (2012).

21. Mevissen, T. E. T. & Komander, D. Mechanisms of Deubiquitinase Specificity and Regulation. *Annu Rev Biochem* 86, 159-192, doi:10.1146/annurev-biochem-061516-044916 (2017).

22. Mevissen, T. E. et al. OTU deubiquitinases reveal mechanisms of linkage specificity and enable ubiquitin chain restriction analysis. *Cell* 154, 169-184, doi:10.1016/j.cell.2013.05.046 (2013).

23. Jespersen, T. et al. The KCNQ1 potassium channel is down-regulated by ubiquitylating enzymes of the Nedd4/Nedd4-like family. *Cardiovasc Res* 74, 64-74, doi:10.1016/j.cardiores.2007.01.008 (2007).

24. Krzystanek, K. et al. Deubiquitylating enzyme USP2 counteracts Nedd4-2-mediated downregulation of KCNQ1 potassium channels. *Heart Rhythm* 9, 440-448, doi:10.1016/j.hrthm.2011.10.026 (2012).

25. Albesa, M., Grilo, L. S., Gavillet, B. & Abriel, H. Nedd4-2-dependent ubiquitylation and regulation of the cardiac potassium channel hERG1. *J Mol Cell Cardiol* 51, 90-98, doi:10.1016/j.yjmcc.2011.03.015 (2011).

26. Hantouche, C. et al. Bag1 Co-chaperone Promotes TRC8 E3 Ligase-dependent Degradation of Misfolded Human Ether a Go-Go-related Gene (hERG) Potassium Channels. *J Biol Chem* 292, 2287-2300, doi:10.1074/jbc.M116.752618 (2017).

27. Iwai, C. et al. Hsp90 prevents interaction between CHIP and HERG proteins to facilitate maturation of wild-type and mutant HERG proteins. *Cardiovasc Res* 100, 520-528, doi:10.1093/cvr/cvt200 (2013).

28. Guo, J. et al. Extracellular K+ concentration controls cell surface density of IKr in rabbit hearts and of the HERG channel in human cell lines. *J Clin Invest* 119, 2745-2757, doi:10.1172/JCI39027 (2009).

29. Massaeli, H., Guo, J., Xu, J. & Zhang, S. Extracellular K+ is a prerequisite for the function and plasma membrane stability of HERG channels. *Circ Res* 106, 1072-1082, doi:10.1161/CIRCRESAHA.109.215970 (2010).

30. Dennis, A. T., Nassal, D., Deschenes, I., Thomas, D. & Ficker, E. Antidepressant-induced ubiquitination and degradation of the cardiac potassium channel hERG. *J Biol Chem* 286, 34413-34425, doi:10.1074/jbc.M111.254367 (2011).

31. Kang, Y., Guo, J., Yang, T., Li, W. & Zhang, S. Regulation of the human ether-a-go-go-related gene (hERG) potassium channel by Nedd4 family interacting proteins (Ndfips). *Biochem J* 472, 71-82, doi:10.1042/BJ20141282 (2015).

32. Schneekloth, J. S., Jr. et al. Chemical genetic control of protein levels: selective in vivo targeted degradation. *J Am Chem Soc* 126, 3748-3754, doi:10.1021/ja039025z (2004).

33. Zhang, M. et al. Chaperoned ubiquitylation-crystal structures of the CHIP U box E3 ubiquitin ligase and a CHIP-Ubc13-Uev1a complex. *Mol Cell* 20, 525-538, doi:10.1016/j.molcel.2005.09.023 (2005).

34. Murata, S., Chiba, T. & Tanaka, K. CHIP: a quality-control E3 ligase collaborating with molecular chaperones. *Int J Biochem Cell Biol* 35, 572-578 (2003).

35. Connell, P. et al. The co-chaperone CHIP regulates protein triage decisions mediated by heat-shock proteins. *Nat Cell Biol* 3, 93-96, doi:10.1038/35050618 (2001).

36. Kubala, M. H., Kovtun, O., Alexandrov, K. & Collins, B. M. Structural and thermodynamic analysis of the GFP: GFP-nanobody complex. *Protein Sci* 19, 2389-2401, doi:10.1002/pro.519 (2010).

37. Wang, M. & Pickart, C. M. Different HECT domain ubiquitin ligases employ distinct mechanisms of polyubiquitin chain synthesis. *EMBO J* 24, 4324-4333, doi:10.1038/sj.emboj.7600895 (2005).

38. Wang, M., Cheng, D., Peng, J. & Pickart, C. M. Molecular determinants of polyubiquitin linkage selection by an HECT ubiquitin ligase. *EMBO J* 25, 1710-1719, doi:10.1038/sj.emboj.7601061 (2006).

39. Scialpi, F. et al. Itch self-polyubiquitylation occurs through lysine-63 linkages. *Biochem Pharmacol* 76, 1515-1521, doi:10.1016/j.bcp.2008.07.028 (2008).

40. Ogunjimi, A. A. et al. The ubiquitin binding region of the Smurf HECT domain facilitates polyubiquitylation and binding of ubiquitylated substrates. *J Biol Chem* 285, 6308-6315, doi:10.1074/jbc.M109.044537 (2010).

41. Kim, H. C. & Huibregtse, J. M. Polyubiquitination by HECT E3s and the determinants of chain type specificity. *Mol Cell Biol* 29, 3307-3318, doi:10.1128/MCB.00240-09 (2009).

42. Scheffner, M. & Kumar, S. Mammalian HECT ubiquitin-protein ligases: biological and pathophysiological aspects. *Biochim Biophys Acta* 1843, 61-74, doi:10.1016/j.bbamcr.2013.03.024 (2014).

43. Michel, M. A. et al. Assembly and specific recognition of k29- and k33-linked polyubiquitin. *Mol Cell* 58, 95-109, doi:10.1016/j.molcel.2015.01.042 (2015).

44. Matsumoto, M. L. et al. K11-linked polyubiquitination in cell cycle control revealed by a K11 linkagespecific antibody. *Mol Cell* 39, 477-484, doi:10.1016/j.molcel.2010.07.001 (2010).

45. Newton, K. et al. Ubiquitin chain editing revealed by polyubiquitin linkage-specific antibodies. *Cell* 134, 668-678, doi:10.1016/j.cell.2008.07.039 (2008).

46. Crabtree, G. R. & Schreiber, S. L. Three-part inventions: intracellular signaling and induced proximity. *Trends Biochem Sci* 21, 418-422, doi:S0968-0004(96)20027-1 [pii](1996).
47. Inoue, T., Heo, W. D., Grimley, J. S., Wandless, T. J. & Meyer, T. An inducible translocation strategy to rapidly activate and inhibit small GTPase signaling pathways. *Nat Methods* 2, 415-418, doi:nmeth763 [pii] 10.1038/nmeth763 (2005).
48. Yang, T., Suhail, Y., Dalton, S., Kernan, T. & Colecraft, H. M. Genetically encoded molecules for inducibly inactivating CaV channels. *Nat Chem Biol* 3, 795-804, doi:nchembio.2007.42 [pii] 10.1038/nchembio.2007.42 (2007).
49. Stornaiuolo, M. et al. KDEL and KKXX retrieval signals appended to the same reporter protein determine different trafficking between endoplasmic reticulum, intermediate compartment, and Golgi complex. *Mol Biol Cell* 14, 889-902, doi:10.1091/mbc.E02-08-0468 (2003).
50. Lee, S. A. et al. Targeting of the FYVE domain to endosomal membranes is regulated by a histidine switch. *Proc Natl Acad Sci USA* 102, 13052-13057, doi:10.1073/pnas.0503900102 (2005).
51. Maffucci, T. & Falasca, M. Specificity in pleckstrin homology (PH) domain membrane targeting: a role for a phosphoinositide-protein co-operative mechanism. *FEBS Lett* 506, 173-179 (2001).
52. Mevissen, T. E. T. et al. Molecular basis of Lys11-polyubiquitin specificity in the deubiquitinase Cezanne. *Nature* 538, 402-405, doi:10.1038/nature19836 (2016).
53. Damgaard, R. B. et al. The Deubiquitinase OTULIN Is an Essential Negative Regulator of Inflammation and Autoimmunity. *Cell* 166, 1215-1230 e1220, doi:10.1016/j.cell.2016.07.019 (2016).
54. Ordureau, A., Munch, C. & Harper, J. W. Quantifying ubiquitin signaling. *Mol Cell* 58, 660-676, doi:10.1016/j.molcel.2015.02.020 (2015).

What is claimed is:

1. A vector comprising a nucleic acid molecule encoding a recombinant engineered deubiquitinase (DUB) comprising:
   a) a catalytic unit comprising the catalytic domain of a deubiquitinase;
   b) a protein binder comprising an antibody, or antigen binding fragment thereof, that specifically binds a target substrate protein for deubiquitination by the engineered DUB; and
   c) a variable linker between the catalytic unit and the protein binder.
2. The vector of claim 1, wherein the vector is a plasmid vector.
3. The vector of claim 1, wherein the vector is a viral vector.
4. The vector of claim 3, wherein the viral vector is an adenoviral vector.
5. The vector of claim 1, wherein the nucleic acid molecule is an RNA molecule.
6. The vector of claim 1, wherein the nucleic acid molecule is an mRNA molecule.
7. The vector of claim 1, wherein the nucleic acid molecule is an DNA molecule.
8. The vector of claim 1, wherein the nucleic acid molecule is a cDNA molecule.
9. The vector of claim 1, wherein the catalytic unit comprises the catalytic domain of a deubiquitinase, wherein the deubiquitinase is from the ubiquitin specific proteases (USP) family, the ovarian tumor proteases (OTU) family, the ubiquitin C-terminal hydrolases (UCH) family, the Josephin domain (Josephin) family, the motif interacting with ubiquitin-containing novel DUB (MINDY) family, or the JAB1/MPN/Mov34 metalloenzyme domain (JAMM) family.
10. The vector of claim 1, wherein the catalytic unit comprises the catalytic domain of a deubiquitinase from the USP family.
11. The vector of claim 1, wherein the catalytic unit comprises the catalytic domain of USP21.
12. The vector of claim 1, wherein the catalytic unit comprises the catalytic domain of a deubiquitinase from the OTU family.
13. The vector of claim 1, wherein the catalytic unit comprises the catalytic domain of OTUD1 or OTUD4.
14. The vector of claim 1, wherein the catalytic unit comprises the catalytic domain of Cezanne.
15. The vector of claim 1, wherein the catalytic unit comprises the catalytic domain of TRABID.
16. The vector of claim 1, wherein the catalytic unit comprises the catalytic domain of OTULIN.
17. The vector of claim 1, wherein the catalytic unit comprises the catalytic domain of USP21 and is capable of non-selectively eliminating all ubiquitin linkage types.
18. The vector of claim 1, wherein the catalytic unit comprises the catalytic domain of OTUD1 and is capable of selectively eliminating K63 ubiquitin linkages.
19. The vector of claim 1, wherein the catalytic unit comprises the catalytic domain of OTUD4 and is capable of selectively eliminating K48 ubiquitin linkages.
20. The vector of claim 1, wherein the catalytic unit comprises the catalytic domain of Cezanne and is capable of selectively eliminating K11 ubiquitin linkages.
21. The vector of claim 1, wherein the catalytic unit comprises the catalytic domain of TRABID and is capable of selectively eliminating K29 ubiquitin linkages, K33 ubiquitin linkages, or K29 and K33 ubiquitin linkages.
22. The vector of claim 1, wherein the catalytic unit comprises the catalytic domain of OTULIN and is capable of selectively eliminating Met1 ubiquitin linkages.
23. The vector of claim 1, wherein the antibody is a nanobody, scFv, (scFv)2, Fab, Fab', F(ab')2, Fv, diabody, or a DARPin.
24. The vector of claim 1, wherein the antibody is a scFv, (scFv)2, Fab, Fab', F(ab')2, Fv, antibody mimetic, or diabody.
25. The vector of claim 1, wherein the antibody is a single domain antibody (dAb).
26. The vector of claim 1, wherein the antibody is a nanobody.
27. The vector of claim 1, wherein the catalytic unit comprises the catalytic domain of Cezanne and the antibody is a nanobody.
28. The vector of claim 1, wherein the catalytic unit comprises the catalytic domain of Cezanne and the antibody is a single domain antibody (dAb).
29. The vector of claim 1, wherein the protein binder specifically binds an ion channel.
30. The vector of claim 29, wherein the ion channel is KCNQ1, HERG, or CFTR.

* * * * *